US011840682B2

(12) United States Patent
Valat et al.

(10) Patent No.: US 11,840,682 B2
(45) Date of Patent: Dec. 12, 2023

(54) CELL CULTURE CASSETTE AND AUTOMATED APPARATUS

(71) Applicant: CellProthera, Mulhouse (FR)

(72) Inventors: Christophe Valat, Mulhouse (FR); Philippe Henon, Mulhouse (FR); Claire Saucourt, Mulhouse (FR); Raoul Weil, Dorlisheim (FR); Jérôme Serre, Pertuis (FR); Cyrille Marechal, Billom (FR)

(73) Assignee: CELLPROTHERA, Mulhouse (FR)

( * ) Notice: Subject to any disclaimer, the term of this patent is extended or adjusted under 35 U.S.C. 154(b) by 442 days.

(21) Appl. No.: 16/312,434

(22) PCT Filed: Jun. 26, 2017

(86) PCT No.: PCT/FR2017/051703
§ 371 (c)(1),
(2) Date: Dec. 21, 2018

(87) PCT Pub. No.: WO2017/220948
PCT Pub. Date: Dec. 28, 2017

(65) Prior Publication Data
US 2019/0241851 A1 Aug. 8, 2019

(30) Foreign Application Priority Data
Jun. 24, 2016 (FR) ...................................... 1655922

(51) Int. Cl.
*C12M 1/00* (2006.01)
*C12M 3/06* (2006.01)
(Continued)

(52) U.S. Cl.
CPC ............ *C12M 23/14* (2013.01); *C12M 21/00* (2013.01); *C12M 23/24* (2013.01); *C12M 23/40* (2013.01); *C12M 23/48* (2013.01); *C12M 27/16* (2013.01)

(58) Field of Classification Search
CPC ........ C12M 23/14; C12M 41/14; F16K 7/065
See application file for complete search history.

(56) References Cited

U.S. PATENT DOCUMENTS 3,232,568 A * 2/1966 Lennon ................... F16K 27/00
248/67
5,988,422 A * 11/1999 Vallot ..................... C12M 23/14
220/62.22
(Continued)

FOREIGN PATENT DOCUMENTS

DE  10 2014 105472   8/2000
JP  A-H11-507229    6/1999
(Continued)

OTHER PUBLICATIONS

International Search Report and Written Opinion for Application No. PCT/FR2017/051703 dated Oct. 30, 2017, 8 pages.
(Continued)

*Primary Examiner* — Jonathan M Hurst
(74) *Attorney, Agent, or Firm* — Alston & Bird LLP

(57) ABSTRACT

The invention concerns a cassette for cell culture comprising: an at least partially rigid housing internally defining an internal space inside which a cell culture bag defining an internal volume is arranged and attached; conduits each connected at one end to the internal volume of the bag and each having a second end situated outside the housing; and valves for enabling/preventing the flow of fluid through the conduits that are mounted on the housing.

31 Claims, 12 Drawing Sheets

(51) Int. Cl.
*C12M 1/04* (2006.01)
*C12M 3/00* (2006.01)

(56) References Cited

U.S. PATENT DOCUMENTS

| | | | |
|---|---|---|---|
| 6,082,702 A * | 7/2000 | Campau | F16K 7/061 251/8 |
| 6,096,532 A | 8/2000 | Armstrong et al. | |
| 6,786,054 B2 * | 9/2004 | Voute | F25D 31/001 62/356 |
| 7,350,537 B2 * | 4/2008 | Honermann | A01C 23/008 137/343 |
| 8,028,532 B2 * | 10/2011 | Voute | A61J 1/165 62/66 |
| 8,448,457 B2 * | 5/2013 | Cutting | A01N 1/0252 62/530 |
| 2005/0011202 A1 * | 1/2005 | Voute | F25D 31/001 62/62 |
| 2010/0316446 A1 * | 12/2010 | Runyon | C12M 41/14 405/128.45 |
| 2011/0198255 A1 * | 8/2011 | Baumfalk | G01N 33/48785 206/459.1 |
| 2012/0308531 A1 | 12/2012 | Pinxteren et al. | |
| 2013/0058907 A1 | 3/2013 | Wojciechowski et al. | |
| 2013/0078721 A1 | 3/2013 | Douay et al. | |
| 2013/0244322 A1 * | 9/2013 | Henon | C12M 27/10 435/325 |
| 2013/0308531 A1 | 11/2013 | So et al. | |
| 2014/0087455 A1 * | 3/2014 | Kobayashi | C12M 23/14 435/294.1 |
| 2017/0036181 A1 | 2/2017 | Boettcher et al. | |

FOREIGN PATENT DOCUMENTS

| | | |
|---|---|---|
| JP | A-2004-251292 | 9/2004 |
| WO | WO-1996/040858 | 12/1996 |
| WO | WO 2011/101468 | 8/2011 |
| WO | WO 2013/135817 | 9/2013 |

OTHER PUBLICATIONS

Translation of Written Opinion for International Application No. PCT/FR2017/051703 dated Oct. 30, 2017 (of document previously submitted), 5 pages.

Iscove, N. N. et al., *Complete Replacement of Serum by Albumin, Transferrin, and Soybeam Lipid In Cultures of Lipopolysacchride-Reactive B Lymphocytes*, J. Exper. Med., vol. 147 (1978) 923-933.

*Functional Capacity and Object Assessment*, Nomenclature and Criteria for Diagnosis of Diseases of the Heart and Great Vessels, [The Criteria Committee of the New York Heart Association] ($9^{th}$ edition) Boston: Little, Brown & Co., (1994) 253-256.

* cited by examiner

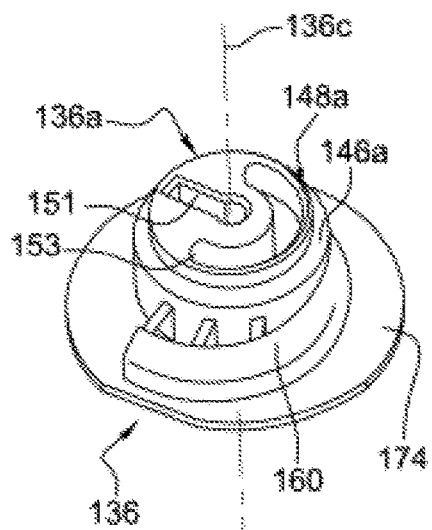
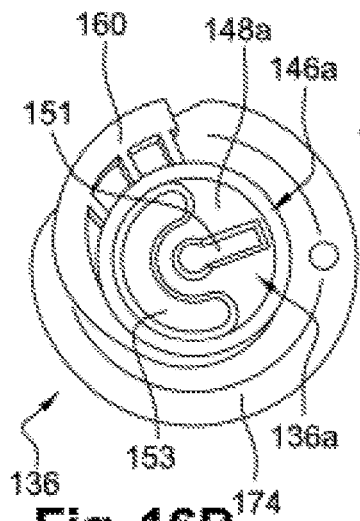
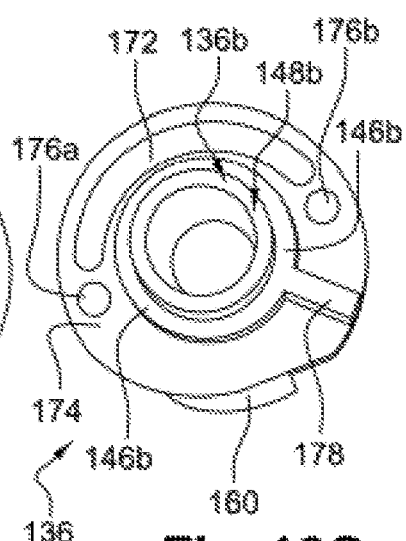
Fig. 16A     Fig. 16B     Fig. 16C
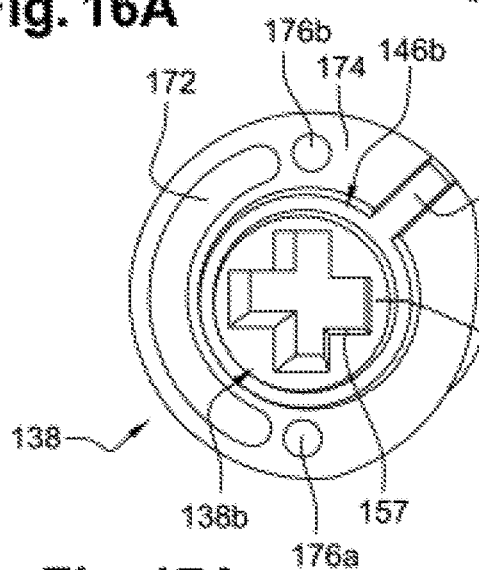
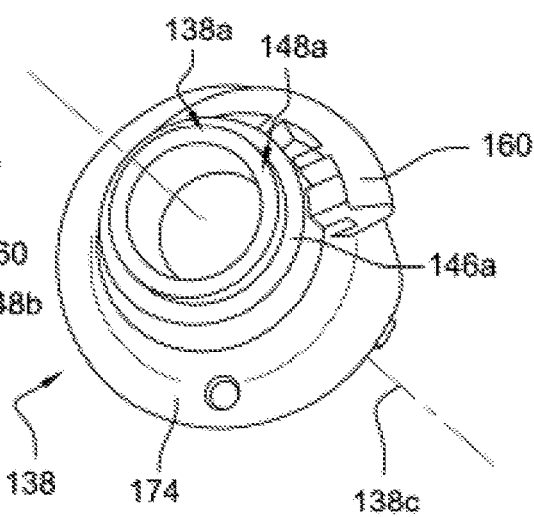
Fig. 17A     Fig. 17B
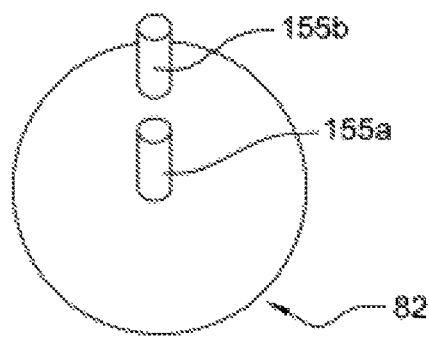
Fig. 18

CELL CULTURE CASSETTE AND AUTOMATED APPARATUS

FIELD

This invention related to a cell culture cassette, as well as a cell culture automated apparatus using said cassette. The invention thus concerns a device for cell culture, referred to as a cassette.

BACKGROUND

Among the fields using cell culture, cell therapy is the least advanced in terms of industrialization. There is therefore an important need to find a technology capable of producing cells in sufficient quantity and under optimal and safe conditions for the use of these cells for therapeutic applications.

Some cell therapy processes require a culture or amplification of stem cells before they are reinjected into a patient, as the quantities collected are sometimes insufficient to have a therapeutic effect. It is essential to guarantee the integrity of the therapeutic properties of the cells during their culture. In the current technique, the solutions proposed for culturing stem cells ex vivo are artisanal, very empirical and poorly effective.

In addition, current technology does not allow stem cells to be produced in sufficient quantities for therapeutic applications. There is therefore a real need to develop a bioreactor technology with a compact geometry and which allows cells to be grown in large quantities.

The automation of stem cell expansion processes for production applications in therapeutic or clinical settings requires cell production devices capable of operating in controlled activity areas (clean room), with minimal human intervention. Stem cell culture processes are relatively complex because they involve multiple steps for obtaining these cells from a patient's sample, isolating the cells, purifying before culturing and finally collecting, purifying and packaging the cells after culture before sending them to clinical treatment centres.

All these steps must be carried out in accordance with manufacturing standards imposing stringent sterility and traceability conditions. The multiplication of manufacturing steps, often manual, requires the use of containment areas of different classes in order to maintain process sterility. The proper conduct of the preparation process before and after cultivation often involves the transfer of process intermediates from one area to another, increasing both the risk of sterility loss and the risk of mixing production flows.

For example, a cell culture system such as that described in document US2012/0308531 is known. The production of continuous cultures for stem cell production is carried out by means of a complex system of sub-assemblies bringing the different reagents, cells and gases to the reactor.

The applicant has also proposed an automated apparatus for automated cell culture in document WO/2013/135817. If the cell culture is carried out within a single pocket, its handling can be difficult due to its flexible structure.

The purpose of this invention is in particular to provide a simple, effective and economical solution to the problems of the prior art described above.

SUMMARY

To this end, it proposes a cell culture cassette comprising:
an at least partially rigid housing and defining an inner space in which a cell culture bag defining an inner volume is arranged and fixed,
ducts each connected at one end to the inner volume of the pocket and each having a second end located outside the housing, and
valves to open/close the fluid flow through the conduits that are mounted on the housing.

The pocket and valves are handled through the cassette housing. Only the second ends of the ducts require direct handling. According to the invention, the cell culture cassette or device integrates all the elements likely to pose a difficulty in terms of sterility and whose direct handling must be limited. These elements are pre-assembled in a single-use cell culture cassette. After use, it is possible to dispose of all the used conduits, valves and culture bags according to the rules of good practice. Preferably, the integration of a flexible pocket in an at least partially rigid housing greatly facilitates the handling of the pocket, which is thus retained in the housing. Similarly, the integration of the valves in the housing makes it easier to identify the valve positions, which can then be more easily handles by incubator control means, as will appear in the following description.

The solution for integrating the valves into the fluid cassette as a means of occluding the cassette lines makes it possible to improve the automation of the use of the cassette in a cell culture process by avoiding the use of plastic "clamps", often weakened during a freezing step, and operable only by hand, or of pinch solenoid valves requiring the manual installation of the lines in the solenoid valve jaw. This solution therefore avoids the manipulation of the conduits, and errors related to the incorrect insertion of the conduits into the solenoid valves.

The cassette in which the bag contains a cell culture medium can be frozen for as long as necessary.

Another feature of the invention is that the conduits are formed by flexible tubing and at least some of the valves includes a movable pinch member for the tubing on a structural element of the housing. As described above, the integration of the valves in the cassette allows the closed tracks (storage or cultivation time) to be kept autonomous and secure for a desired time without the need for the external energy.

According to yet another characteristic of the invention, each movable member includes an axis of rotation and the radially outer periphery of each movable member includes at least one spiral surface about the axis of rotation forming a pinch surface of the tubing so as to vary a fluid passage section through a tubing as the member rotates.

Advantageously, the valves are able to maintain a given position. More specifically, the valves are designed in such a way that the moving parts can maintain a given opening or closing position in the absence of energy supply. In particular, this can be achieved by ensuring that the perpendicular to the point of contact of the spiral surface with a tubing is oriented towards the axis of rotation of the moving member, resulting in zero torque about said axis.

In a particular design, the movable parts are mounted in recesses of a plate fixed to the housing, each recess receiving a movable part. When the housing is made of two lower and upper half-shells, it is thus possible to mount the cell culture bag on the lower half-shell, to mount the movable parts for pinching the tubing on the lower half-shell and then to mount the plate which ensures simultaneous holding of the movable parts. The plate can, for example, be attached to the lower half-shell for example by screws. The plate thus makes it possible to secure and facilitate the assembly of the various parts mentioned above. It ensures that the valves are maintained.

Each movable member includes an end accessible from outside the housing and provided with first rotational coupling means intended to cooperate with second rotational coupling means of an actuator which can be electromechanical.

Access to the movable parts of the valves from the outside makes it possible to mount the cassette on a suitable support of an incubator comprising second coupling means, for example, complementary second coupling means for rotating the first valve coupling means to open/close the liquid circulation as required. This external accessibility makes it possible to manually handle the valves in the event of failure of the valve drive means.

Preferably, the moving parts are centred and guided in a rotating manner at one end located in an opening of the housing and at an opposite end located in an opening of the plate. When the housing consists of two half-shells, the plate can be clamped inside the housing between these two half-shells.

According to another characteristic of the invention, the pouch has a substantially rectangular shape with a first flexible wall and a second flexible wall substantially parallel to each other in the empty and liquid-filled state.

The rectangular shape is substantially flat so that the thickness measured between the first and second walls, in a first direction substantially perpendicular to the first and second walls, is very small, i.e. very much smaller than the other two dimensions of the pocket measured in the other two directions of the space perpendicular to each other and to said first direction. "Very significantly inferior" means at least 10 times inferior, as commonly accepted in mathematics.

Preferably, the ratio of the sum of the surfaces of the first and second walls to the total internal volume of the bag is between 500 and 690 $cm^2/L$, preferably in the order of 580 $cm^2/L$. This ratio ensures optimal heat exchange between the flexible bag and the outside when the cassette is placed within an incubator in a thermostatic enclosure.

The distance between the first wall and the second wall or thickness of the pouch in the liquid-filled state, measured in a direction perpendicular to the first and second walls, is advantageously less than 20 mm, preferably between 10 and 20 mm and even more preferably in the order of 14 mm. The use of a thin thickness further facilitates the diffusion of heat within the liquid in the bag. This also allows for uniform freezing and thawing of the different components of the culture medium, which is quicker at constant temperature.

The bag according to the invention makes it possible to maintain the stability of the culture medium during a freezing step by deep freezing. Indeed, a high freezing rate of biological products derived from blood is a guarantee of preservation of constituents, homogeneity of the medium after thawing, and absence of concentration effect of salts and proteins in solution in the heart of the frozen mass. The bag according to the invention promotes rapid freezing of the culture medium thanks to its particular geometry with a high surface-to-volume ratio and low thickness.

According to another characteristic of the invention, the walls of the bag are permeable to gases, in particular $CO_2$, and preferably have properties that limit the adherence of the cells to the bag walls as much as possible.

The pouch is preferably flexible, i.e. deformable. It preferably includes flexible gas-permeable walls capable of retaining the culture medium and its cellular expansion, which is liquid. In practice, it is a matter of retaining any liquid contained in the bag. It preferably has good oxygen and carbon dioxide permeability, which allows good aeration of the contents of the bag without opening it and therefore without risk of contaminating its contents. In a particular embodiment of the invention, the bag includes the following permeability characteristics (in $cm^3$ per day at a pressure of one atmosphere, i. e. 1 bar, at 37° C.): for oxygen 418 to 508, for carbon dioxide 699 to 1200, for nitrogen 157 to 200 and for water 0.05 to 0.1.

The bag is made of a thin film which can be made of copolymer such as fluoropolymer and more particularly of fluorethylene propylene with a thickness of about 120 pm for example. In a preferred embodiment, the bag has a substantially rectangular shape with a thin thickness and may reach a width of 230 to 250 mm maximum flat and a length of 230 to 250 mm flat.

The use of a material belonging to the fluoropolymer family has the advantage of being permeable to gases and also of having a low adhesion to liquids.

The housing shall preferably have a shape substantially corresponding to that of a rectangular parellelepiped and may comprise a lower half-shell and an upper half-shell fixed with each other, the lower half-shell being rigid and the upper half-shell being rigid or flexible.

Thus, the housing can also have a substantially flat shape with a very slim thickness compared to its length and width.

The housing can be made of any elastomer thermoplastic material such as SEBS (Styrene-Ethylene-Butadiene-Styrene). The lower half shell may be rigid to ensure optimal retention of the flexible bag while the upper half shell may be partially rigid and include one or more flexible zones made of an elastomer material to facilitate gripping and some deformability to facilitate assembly of the cassette in the support and agitating means, which will be described below. Of course, the upper half-shell can also be totally rigid like the lower half-shell.

Both the lower and upper half-shells can be assembled by clipping, gluing or welding their peripheral edges. The half-shells can have the same or different thicknesses.

In a preferred embodiment of the invention, the upper half shell may include a central opening or recess, the shape and size of which are designed so as to allow the propagation of a wave of the liquid from the bag into the opening when the cassette containing a liquid is oscillated about a horizontal axis, the opening being configured facing up. The formation of a wave is desirable to achieve rapid homogenization of the liquid in the bag. The formation of a recess, which could also be called a cut-out or an opening, thus avoids having to increase the thickness of the housing. This recess also ensure a better diffusion of gases in contact with the bag. It can have a dimension of about 210 mm wide and about 28 mm long.

Preferably, the lower half shell has a plurality of holes, preferably with a diameter of less than 20 mm, for example. The integration of orifices facilitates the transfer of gas in a similar way to the opening of the upper half-shell while ensuring that the bag is held on the lower half-shell.

In a practical embodiment of the invention, the lower half-shell may include about 60 and 400 orifices each with a diameter between 5 and 20 mm, for example of the order of 10 mm. The holes can be distributed according to a mesh size with a basic pattern that is that of an equilateral triangle with a unit length of between 5 and 40 mm and, for example, of 20 mm.

In a cassette design according to the invention, the conduits extend through one of the peripheral edges of one of the lower or upper half-shells. The ducts can be housed in slots in one of the peripheral edges of a lower or upper half-shell.

The cassette preferably includes a duct support strip, arranged outside the housing and through which at least some of the ducts pass. This strip supports the conduits that extend outside the cassette housing, which limits unintentional movements of the free ends of the conduits. In addition, the support is intended to form a watertight passage element for the door of an incubator as it will better appear in the following description.

The cassette preferably includes a cell culture medium stored in the bag, the cell culture medium can be frozen.

The cell culture medium may be a cell culture medium whose composition is suitable for the multiplication of mammalian cells, in particular human cells, excluding human embryonic stem cells. The culture medium may or may not include cells in culture.

These cells, in particular human cells, excluding human embryonic stem cells, may advantageously be, or include, CD34+ (human) cells, in particular CD34+ (human) hematopoietic cells or non-hematopoietic CD34+ (human) cells. These CD34+ (human) cells may, for example, be cells from peripheral blood (human) or umbilical cord (human) or human tissue, in particular peripheral blood (human).

These cells, in particular human cells, excluding human embryonic stem cells, may advantageously be, or include, stem or progenitor cells, in particular multipotent or pluripotent cells.

These cells are not, or do not include, human embryonic cells.

This cell culture medium may include components that allow these cells to multiply, in particular, that allow them to multiply while maintaining them in an undifferentiated state, or at the very least not reaching a stage of terminal differentiation.

This cell culture medium may include insulin, transferring and plasma or serum (human).

This cell culture medium may include or be devoid of feeder cells, such as fibroblasts.

This cell culture medium may, for example, be, or include, the Iscove's *Modified Dulbecco's Medium* (*IMDM*): see, for example, Iscove, N. N. and Melchers, F. (1978) J. Exper. Med. 147:923), optionally supplemented with glutamine or glutamine-containing peptides.

In particular, this cell culture medium may be, or include, the IMDM medium, optionally supplemented with glutamine or glutamine-containing peptides, which is fibroblast-free and includes human (recombinant) insulin, (human) transferrin and (human) plasma or serum.

For example, the culture medium may include:
from 1 to 50 µg/mL, in particular from 8 to 12 µg/mL, of insulin,
from 100 to 2000 µg/mL, in particular from 300 to 500 µg/mL, transferrin, and
from 1 to 30%, in particular from 4 to 12%, of (human) serum or plasma. The culture medium may also include heparin, for example 1.5 to 3.5 IU/mL of heparin.

The culture medium may also include erythropoietin, including human (recombinant) erythropoietin.

The culture medium may also include one or more growth factors, including one or more growth factors selected from hydrocortisone, SCF (Stem Cell Factor), interleukin 3 (IL-3), thrombopoietin (TOP), FLT3 (Fms-like tyrosine kinase 3), BMP4 (Bone Morphogenetic Protein 4), VEGF-A 165 (Vascular endothelial growth factor A 165), and IL-6.

The culture medium may include, but is not limited to, hydrocortisone, or
SCF, or
SCF and IL-3, or
hydrocortisone and SCF, or
hydrocortisone, SCF and IL-3, or
SCF, TOP, FLT3, BMP4, VEGF-A165, IL-3 and IL-6.

The culture medium may in particular be a culture medium as described in WO 2011/101468 (or in one of the US patent applications that are derived from or based on this international PCT application, such as in particular the US application 2013/0078721 A1, which is incorporated herein by reference).

The cassette may include the culture medium and/or cells as described above.

According to one method of production, the cassette includes the culture medium in the bag, more particularly in frozen form, but does not include cells.

According to another method of production, the cassette includes culture medium in the bag, more particularly in non-frozen form, and also includes cells, in particular cultured cells, in particular CD34+ (human) cells as described above.

The invention also concerns a cell culture incubator, comprising a thermostatic enclosure and a device for supporting and agitating a cell culture cassette according to one of the above claims and means for positioning and blocking the cells culture cassette in a given position in the support device.

In one embodiment, the support and agitation device comprises a support plate for the cell culture cassette which is mounted rotatable about a horizontal axis around which the plate is intended to oscillate for agitating and homogenizing the contents of the bag.

The support and agitation device may include a connecting rod, one upper end of which is connected to the plate via an oscillator and the lower end of which is connected to a crank handle rotatable driven by the shaft of a motor with a substantially horizontal axis.

The incubator may include means for controlling the position of the cell culture cassette in the support means so as to ensure that the cassette is properly positioned on the support means and that is can be used.

The plate can carry electromechanical actuators for opening/closing the valves, one outlet of which carries second coupling means intended to cooperate with first coupling means of the cassette valves when the cassette is in the said given position.

According to another characteristic of the invention, the incubator comprises a door for sealing an opening in the enclosure, this opening comprising a peripheral edge in which a recess is formed, the shape of which is adapted to receive the duct support strip, the strip forming a sealing member between the door and the peripheral edge when the door is in the closing position of the enclosure.

The integration of a duct support strip allows the positioning of the ducts at the doorway to be carried out quickly and easily. Indeed, contrary to the known technique which consists in directly integrating the conduit housing grooves into the peripheral edge, and placing them one by one in grooves, this invention proposes to assemble all the conduits in a single step. In addition, the sealing is carried out on the strip and no longer on the ducts, which makes it easier to carry out the sealing since this strip can have a rigid structure on which the door can be supported.

The invention also concerns a cell culture automated apparatus comprising at least one incubator of the type described above, and a computer control system including data capture and recording means and intended to regulate the culture conditions in an enclosure of said at least one incubator and to control the valves of the cassette housed in the enclosure.

The invention also concerns a process for cell culture by means of the automated apparatus described above, the process comprising the steps of:
  a) placing a cell culture cassette as described above inside the incubator enclosure in a thawing position of the support and agitation device;
  b) supply the bag with cells to be cultivated;
  c) place the cassette on the support and agitation device in a cell culture position;
  d) shake the cell culture cassette for a given period of time to homogenize its contents;
  e) maintain the cell culture cassette under incubation conditions for several days; and
  f) retrieve the contents of the cassette by means of one of the tubes of the cassette.

The process further includes:
  during step d), one or more steps of sampling the contents of the bag, each preceded by a step of tilting the support plate from a horizontal culture position to an inclined position in which the sampling area of the bag represents the lowest point of the bag.

BRIEF DESCRIPTION OF THE DRAWINGS

The invention will be better understood and other details, advantages and characteristics of the invention will appear when reading the following description by way of example, with reference to the annexed drawings in which:

FIGS. 16A, 16B and 16C represent a first variant of a valve that can be used with the plate in FIG. 15A;

FIGS. 17A and 17B represent a second variant of a valve that can be used with the plate in FIG. 15A;

FIG. 18 is a schematic view in perspective of the means of rotating the valve in FIGS. 16A, 16B and 16C;

DETAILED DESCRIPTION

Figure 1:
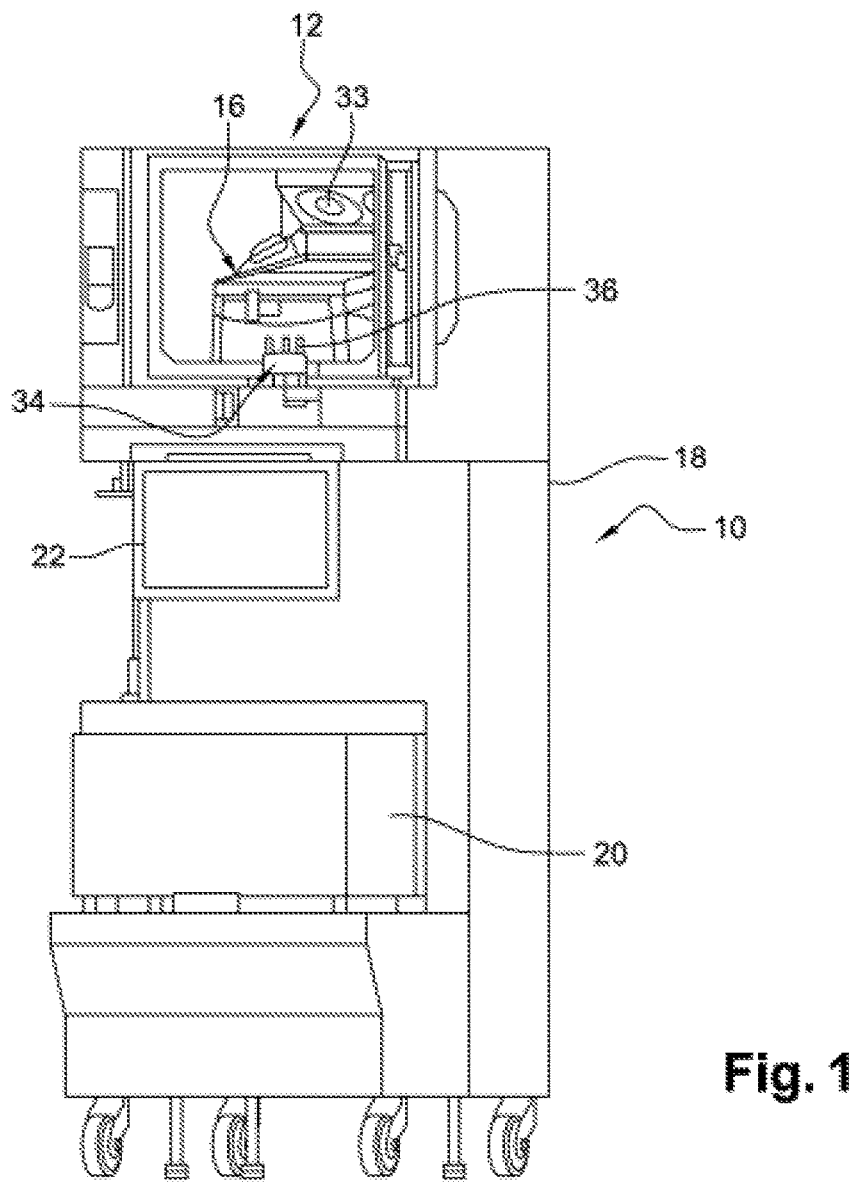
FIG. 1 is a schematic view in perspective of the cell culture automated apparatus according to the invention, this automated apparatus comprising an incubator defining a thermostatically controlled enclosure that is open.
Figure 2:
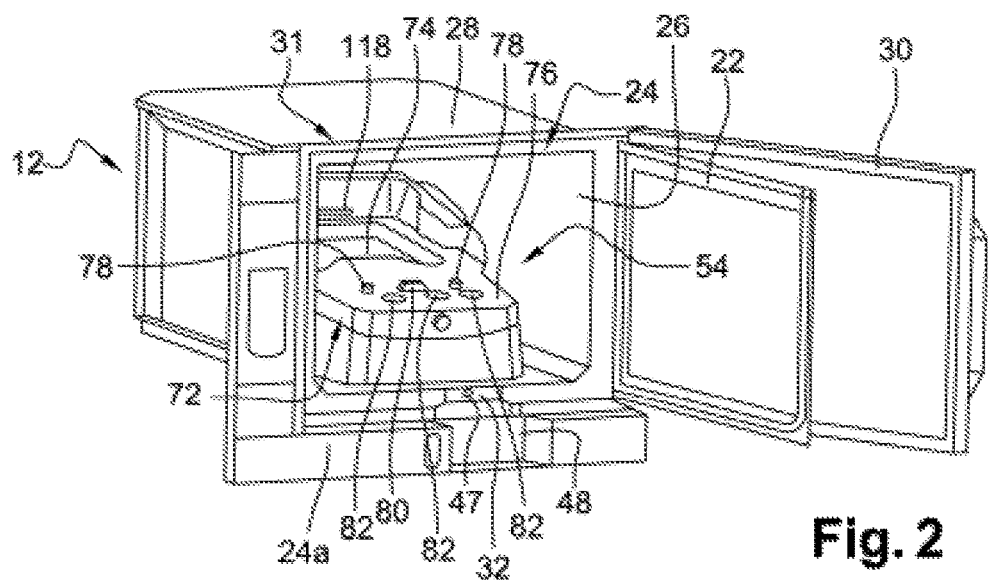
FIG. 2 is a schematic view of the isolated incubator in perspective.

First of all, we refer to FIGS. 1 and 2, which represent an example of an embodiment of the cell culture automated apparatus 10 according to the invention, this automated apparatus 10 being for example intended for the culture of stem cells, to the exclusion of human embryonic stem cells.

As shown, automated apparatus 10 essentially consists of three elements:
  an incubator 12 with a thermostatic enclosure comprising a device for supporting and agitating 14 a cell culture cassette 16 according to the invention (FIGS. 1 and 3);
  a rack 18 supporting the incubator 12 and a centrifuge 20, and
  a computer system connected to the incubator 12 and the centrifuge 20 for valve and pump control and supported by frame 18.

Typically, the computer system includes data entry and recording facilities, data processing facilities, display facilities, and control and monitoring signal transmission facilities for the incubator as well as for valves and pumps of the cassette 16. Preferably, the computer system includes a touch screen display 22 and data entry by an operator or user.

The control and traceability of the biologic protocol steps can be ensured by the computer system and an appropriate human-machine interface (HMI), which allows in particular:
  to ensure full traceability of the manufacturing process of each stem cell graft, the steps of operator intervention on the automated apparatus, culture parameters such as temperature, $CO_2$ rate, and time of each step and the validation actions required at certain process steps,
  to ensure the traceability of consumables and reagents used in the process, via an input interface, means of reading and storing bar code data and RFID labels, and a verification of the consistency of the information collected against an internal database. This traceability can be applied to the entire manufacturing, storage and transport chain of consumables and reagents, as well as to the material conditions for maintaining the temperature of these components.
  to systematically indicate to the user the details of the protocol steps through animations and images illustrating the progress of the process steps,
  securely record patient identification data, biological data related to the characterization of stem cell transplants,
  to control each of the actuator control functions,
  to record and interpret the data of the various sensors present on the automated apparatus or fluidic cassette.

As shown in FIG. 2, incubator 12 has two doors, a first internal door 22 to be applied to a first contact surface surrounding the opening 26 of enclosure 28 of incubator 12 and a second external door 30 to be applied to a second contact surface 31 surrounding the first contact surface 24.

The first door 22 and second door 30 are, for example, each pivotable around the same vertical axis. Enclosure 28 houses ventilation means 33 which are located in the upper part of enclosure 28 (FIGS. 1, 6A, 6B and 6C). These ventilation means 33 are designed and configured to allow a uniform distribution of temperature and gases within the incubator chamber necessary for efficient cell culture and to have an appropriate temperature (FIGS. 1, 6A, 6B and 6C). During thawing of the culture medium contained in the bag, the heat in the chamber is thus uniformly distributed to allow rapid thawing of the cell culture medium.

The internal door 22 can be made of transparent glass so that the contents of the chamber 28 of incubator 12 can be observed while keeping incubator 12 in the closed position. The opening 26 of enclosure 28 includes a peripheral edge 24, corresponding to the first contact surface, whose lower edge 24a includes a recess 32 intended to receive a strip 34 for holding tubes or conduits 36, 38 of cassette 16 which will be described in more detail later, in particular with reference to FIGS. 7 and 8. Bar 34, which is visible in FIGS. 4, 5, 7 and 8, forms a rigid shell that can be substantially parallelepiped in shape. It can also have two flanks 40, opposite and connected to each other by lower and upper sides 42. Ducts or pipes 36, 38 extend water tightly through holes in the strip 34. These holes are formed in walls 44 substantially perpendicular to the flanks 40 and the lower and upper walls 42. Each flank 40 of the bar 34 has a groove 46 parallel to the lower and upper sides 42. The grooves 46 of the flanks 40 are arranged asymmetrically with respect to each other with respect to a median plane of the bar 34 and parallel to both flanks 40. These grooves 46 are intended to receive ribs (not visible) from the sides of recess 32 of the lower peripheral edge 24a of the incubator 12 so as to ensure that the strip 34 is positioned in recess 32. The asymmetrical positioning of the grooves 46 makes it possible to perform a coding when mounting the strip 34 in recess 32 of the incubator 12. Thus, more generally, the strip may include means of coding when mounting it in a recess in a peripheral edge of an incubator opening. The opening can then be closed by a movable member, such as a door or hatch, which is movable between an incubator opening position and an incubator closing position. The bar or rigid shell 34 preferably has a shape complementary to that of the recess 32. This complementary shape may be such that when the strip 34 is in position in recess 32, its lower face 42 contacts the bottom face of recess 32 and the upper face 42 flushes the remainder of the peripheral edge 24 of the opening 26 of the enclosure 28 of incubator 12 to form a substantially flat surface on which the first door 22 can rest in a sealed manner. In this way, the sealing of the inner door 22 on the peripheral edge 24 of the opening 26 of the enclosure 28 of incubator 12 can be carried out in a simple way. In addition, the passage of pipes 36, 38 or ducts through the first door 22 can be easily realized without the need to handle pipes 36, 38 one by one. Finally, when the first door 22 is applied to the strip 34, the closing force is applied to the rigid structure of the strip 34 and not to the pipes 36, 38, which prevents any crushing of the pipes 36, 38 and guarantees their fluid passing cross-section. Preferably, recess 32 may include a presence sensor 47 of the strip 34 to confirm the correct positioning of the strip in recess 32 so as to allow the first door 22 and then the second door 30 to be closed.

As shown in FIG. 2, the front of the incubator chamber 12 has another recess 48 leading into recess 32 of the peripheral edge 24 of opening 26 of enclosure 28. This recess 48 is intended to allow the passage of ducts or pipes 36, 38 beyond recess 32 of the first door 22 and the second door 30 to the centrifuge. In practice, this second recess 48 can be closed by a hatch (not shown), for example a sliding hatch.

Figure 3A:
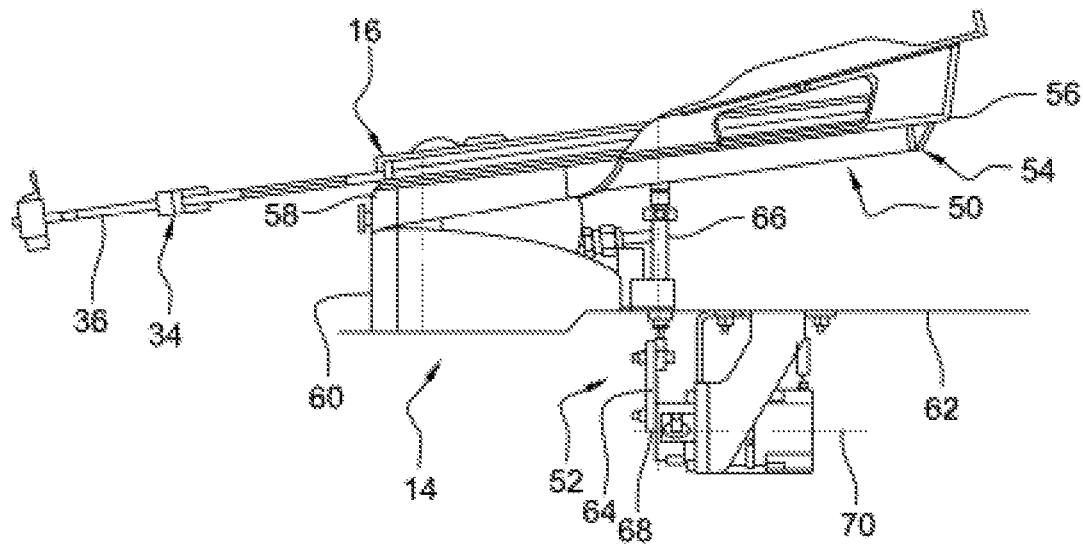
FIGS. 3A and 3B are schematic side views of the support and agitating means and of the cassette.
Figure 3B:
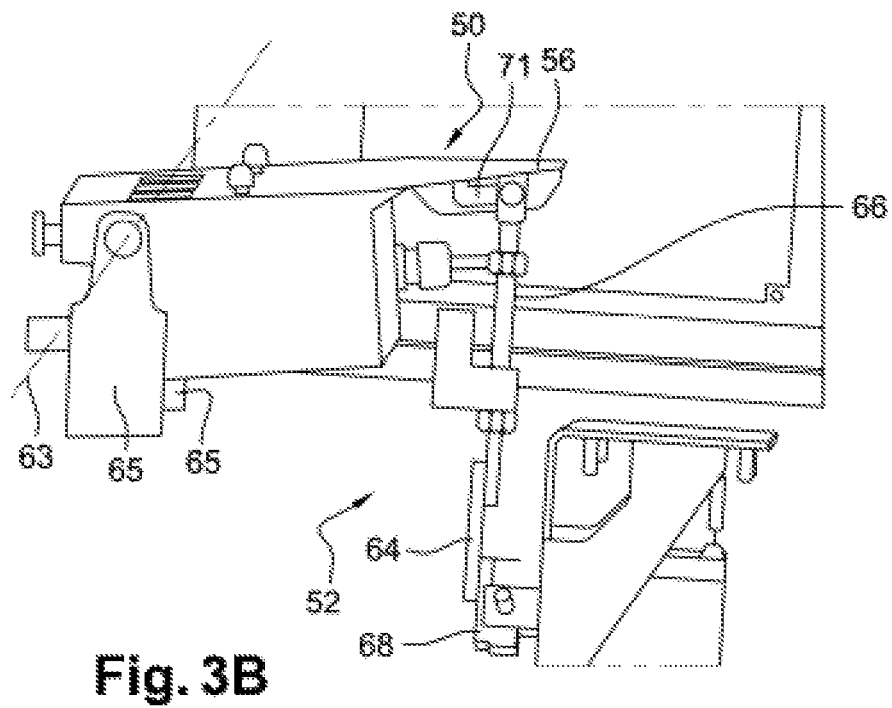
Figure 4:
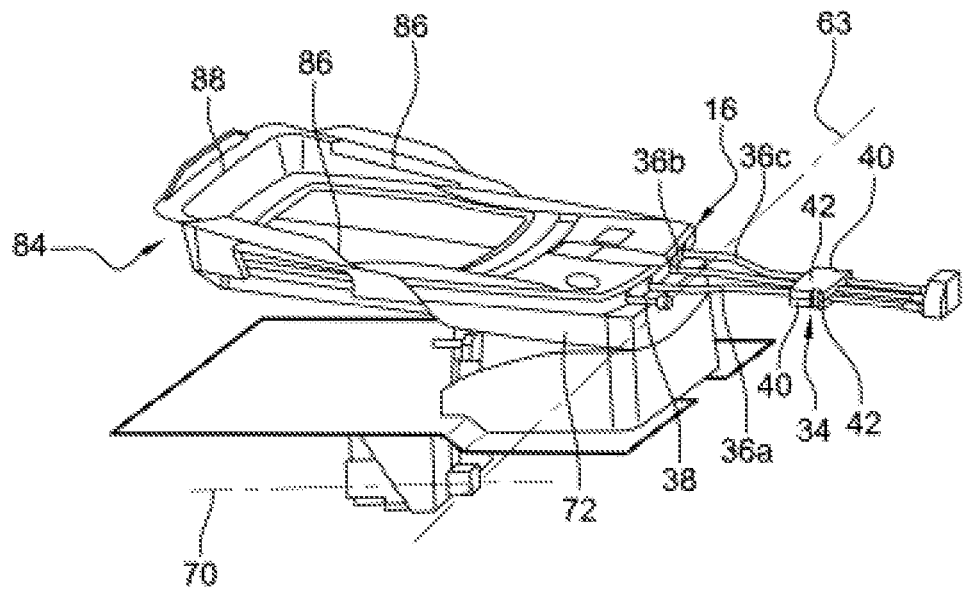
FIG. 4 is a schematic view in perspective of the support and agitation means and of the cassette.

As shown in FIG. 3A, the thermostatic enclosure 28 includes a device for supporting and agitating 14 a cell culture cassette 16 according to the invention. This device can be divided into a support device 50 and a agitation device 52 connected to each other. The support device 50 consists of a support tray 54 or cassette 16 support cradle and a base 60. Plate 54 has a first end 56 located at the bottom of the thermostatic enclosure 28 and a second end 58 opposite the first end which is rotatably connected about a horizontal axis 63 to the substantially vertically extending base 60 and which is carried by the wall 62 forming the floor of the thermostatic enclosure 28 (FIGS. 3A and 4). More precisely and as shown in FIG. 3B, the first end 56 of the plate 54 is carried and rotated about axis 63 on two arms 65 extending vertically from the floor 62 of enclosure 28 and formed on either side of the plate 54.

The agitation device 52 comprises a connecting rod/crank type system having a connecting rod 64, one upper end of which is connected to a lower end of an oscillator or vertical oscillating rod 66 supporting at its opposite upper end the plate 54 by its lower face. The lower end of connecting rod 64 is connected to a crank handle 68 rotatably driven by a motor shaft with a substantially horizontal rotation axis 70. This axis 70 is perpendicular to axis 63. The upper end 66 of the oscillator is connected to the plate so as to allow the oscillator to move in a plane perpendicular to the rotation axis 70. Also, the upper end of the oscillator 66 is movably connected to the support plate 54 in the direction of axis 70, this connection can possibly be made by sliding a finger from the upper end of the oscillator 66 into a slot 71 or groove in the plate 54.

Figure 5:
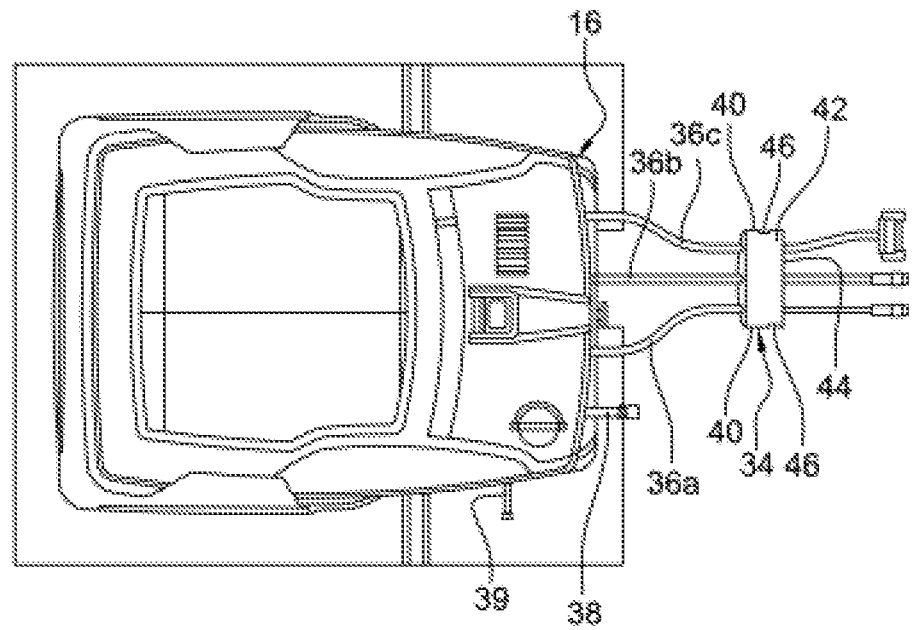
FIG. 5 is a schematic view of the top of the cassette resting on the support and agitation means.

As shown in FIGS. 3, 4 and 5, oscillator 64 passes through the floor wall 62 of enclosure 28 of the incubator 12. Preferably, sealing means, such as a bellows, are provided around the oscillator 66, at the level of the passage area of the floor wall 62 in order to avoid heat and moisture transfers outside the thermostatic enclosure 28 that could damage the mechanical components of the agitation device 52.

Figure 6A:
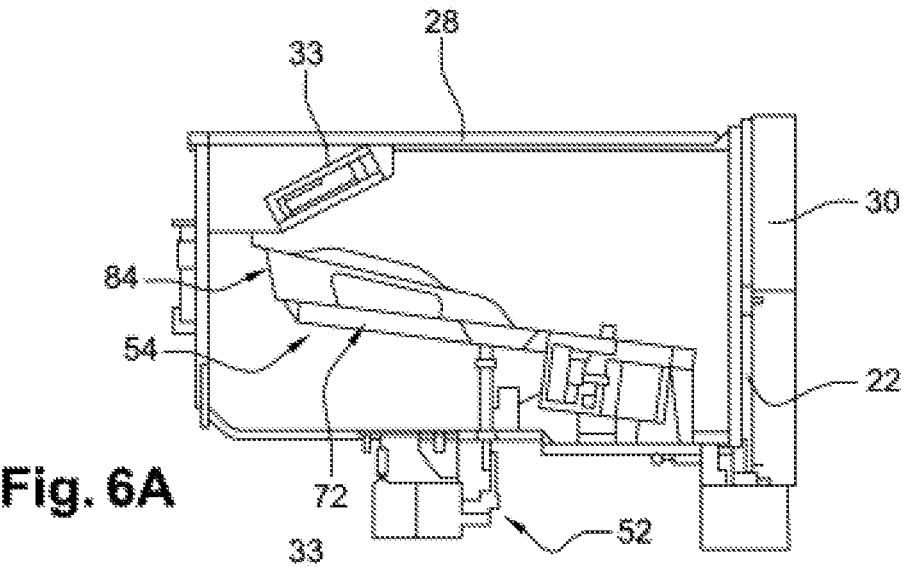
FIGS. 6A to 6C represent different operating positions of the cassette in the thermostatic enclosure of the automated apparatus.
Figure 6B:
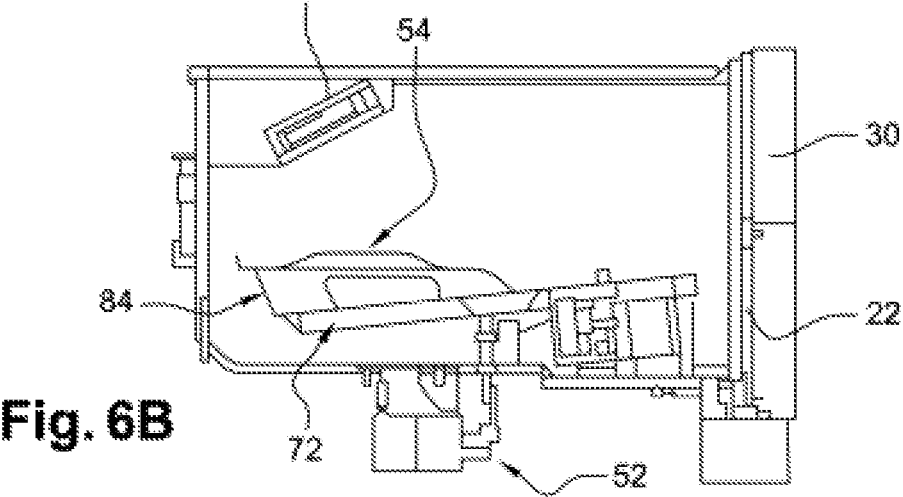
Figure 6C:
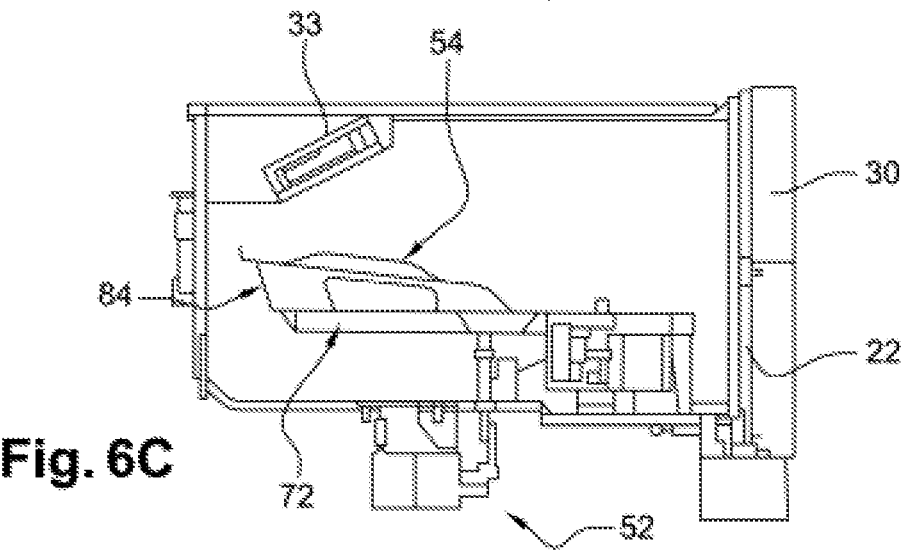

FIGS. 6A, 6B and 6C represent three positions taken by tray 54 during its movement by the agitating means. FIG. 6A shows the tray 54 in its upper position and FIG. 6B shows the tray 54 in its lower position. In either of these two positions the plate is inclined with respect to a horizontal plane. FIG. 6C shows a median position in which the tray 54 is substantially horizontal. During operation, the cassette support plate 54 is thus able to angulate between its extreme positions (FIGS. 6A and 6C) around axis 63 (FIG. 4).

As shown in FIG. 2, the support plate 54 of cassette 16 is formed by a frame 72 with an opening 74 or hollow part and a solid part 76. The hollow part 74, located near the first end 56 of the tray 54, is intended to face the lower half-shell of the cassette, which will be described below. The solid part 76 is arranged in the vicinity of the second end 58 of tray 54. This solid part 76 includes means for positioning and locking the cell culture cassette in a given position on the tray 54 corresponding to a position in which the cassette 16 rests on the frame 72 and allows an incubation phase to be carried out. The positioning means includes two pins 78 projecting upward to cooperate with two blind holes in cassette 16 (described below). The cassette 16 locking means include a clip hook 80 or a snap hook with a cassette hook which will be described below in order to lock cassette 16 on tray 54. The hook 80 of the solid part 46 of the frame 72 of the tray 54 is arranged between the two pins 78.

As shown in FIG. 2, the plate includes three electromechanical actuators 82 for opening/closing valves, each actuator 82 including an output having second coupling means for cooperating with first valve coupling means of the cassette when the cassette 16 rests on the frame 72 of the plate 54.

The frame 72 is surmounted by a structure 84 supporting the cassette 16 at a distance from the frame 72. This support structure 84 allows the cassette 16 to be supported in a second position corresponding to a thawing phase. This support structure 84 comprises two lateral fins 86 connected to each other by a flat wall 88 and together form a common support plane for cassette 16 in the second position. It should be noted that the support planes of cassette 16 in the first position and in the second position are inclined relative to each other. The second position allows the cassette 16, hermetically vacuum sealed in an envelope, to be supported at a distance from the frame 72 in order to avoid any tearing of the envelope, generally made of plastic, by the pins 78 during the thawing phase.

Figure 7:
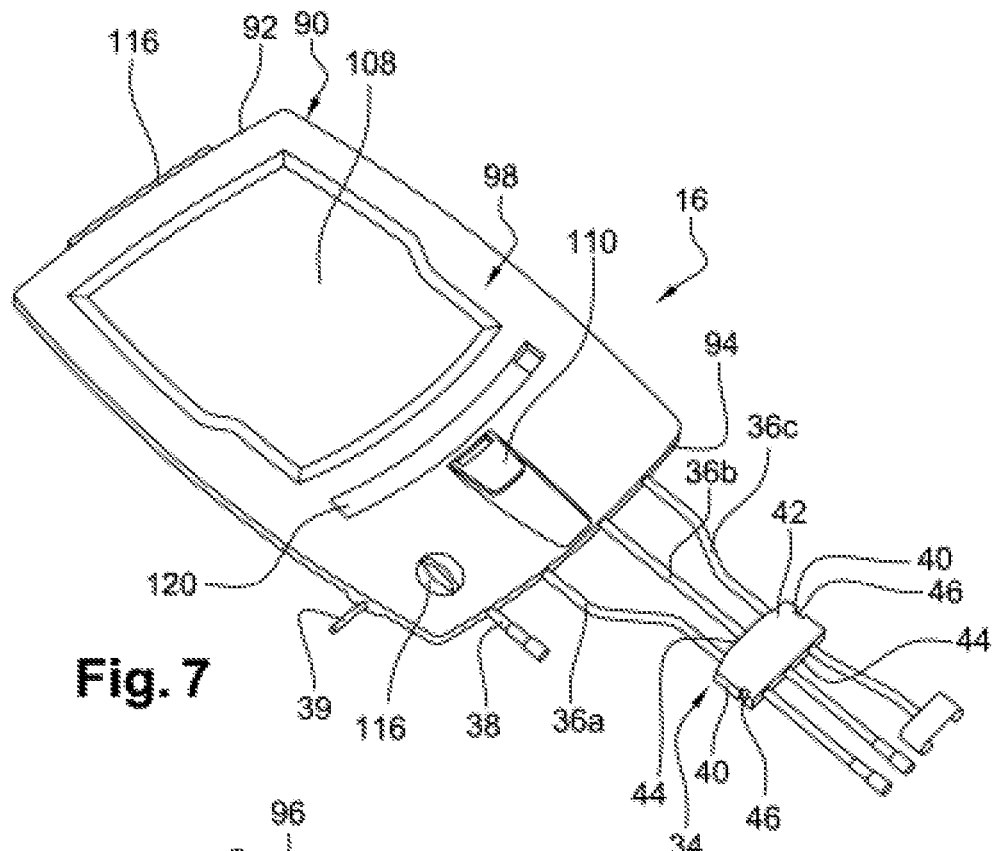
FIG. 7 is a schematic view in perspective of the cassette according to the invention, towards the upper half-shell.
Figure 8:
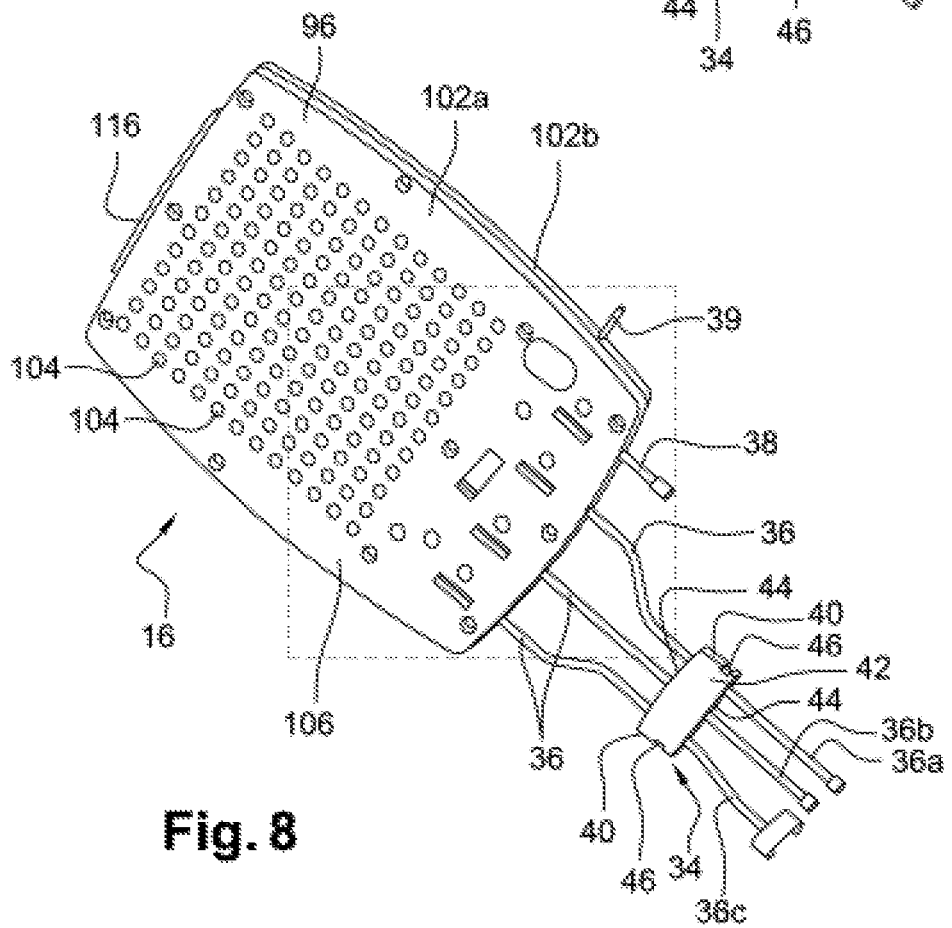
FIG. 8 is a schematic perspective view of the cassette according to the invention, towards the lower half-shell.

FIGS. 7 and 8 are now referred to which represent a cassette 16 for cell culture according to the invention comprising a housing 90 having a shape substantially corresponding to that of a rectangular parallelepiped having a first end 92 and a second end 94 with reference to the positioning of the cassette 16 on the tray 54. The housing 90 has a lower half-shell 96 (FIGS. 9 to 12) and an upper half-shell 98 (FIGS. 13 and 14) integral with each other, the lower half-shell 96 being rigid and the upper half-shell 98 being rigid or partially rigid, i. e. including flexible parts. The two lower half-shell 96 and upper half-shell 98 together define a housing in which is fixed a flexible cell culture bag 100 defining an inner volume to be filled with a cell culture medium.

The lower 96 and upper 98 half-shells are connected to each other by four peripheral edges 102a, 102b. The two lower half-shell 96 and upper half-shell 98 can be assembled by clipping, gluing or welding their peripheral edges 102a, 102b. In a preferred embodiment, the lower half-shell 96 and upper half-shell 98 are both rigid.

Figure 11:
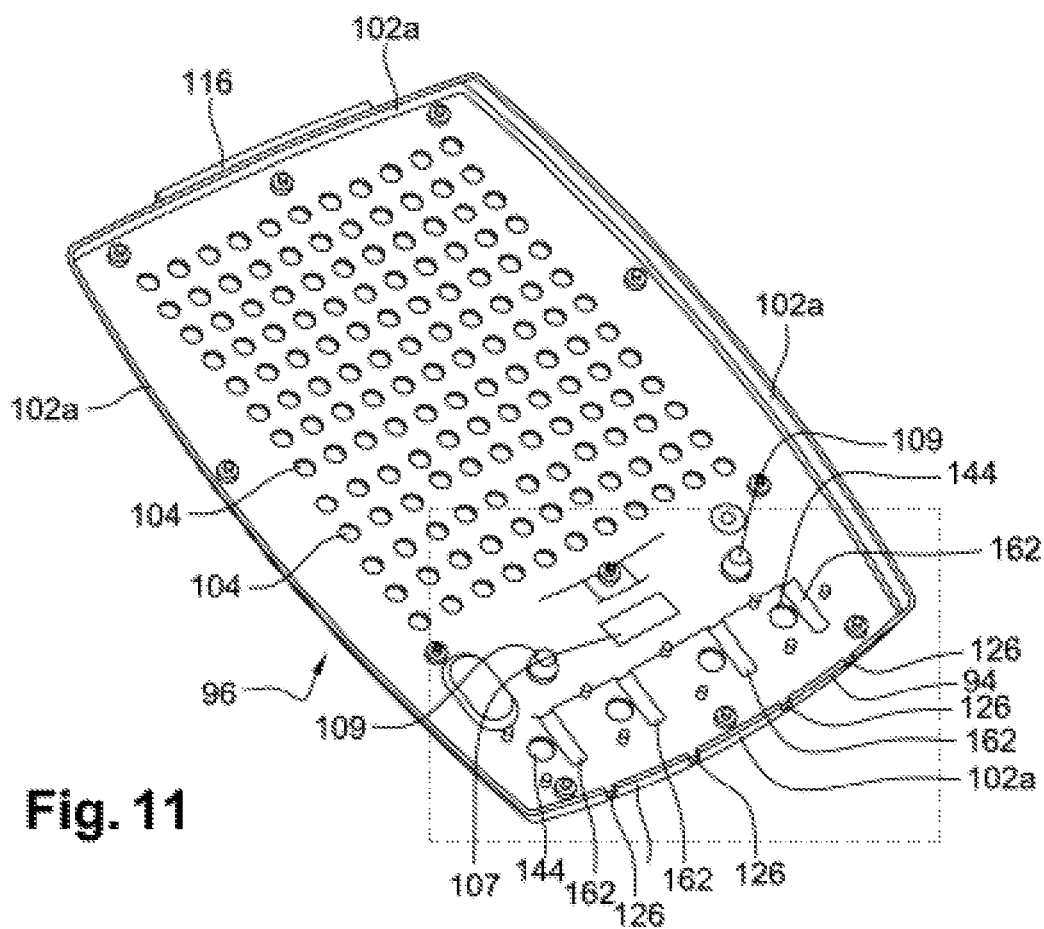
FIG. 11 is an isolated schematic view in perspective of the lower half-shell.
Figure 12:
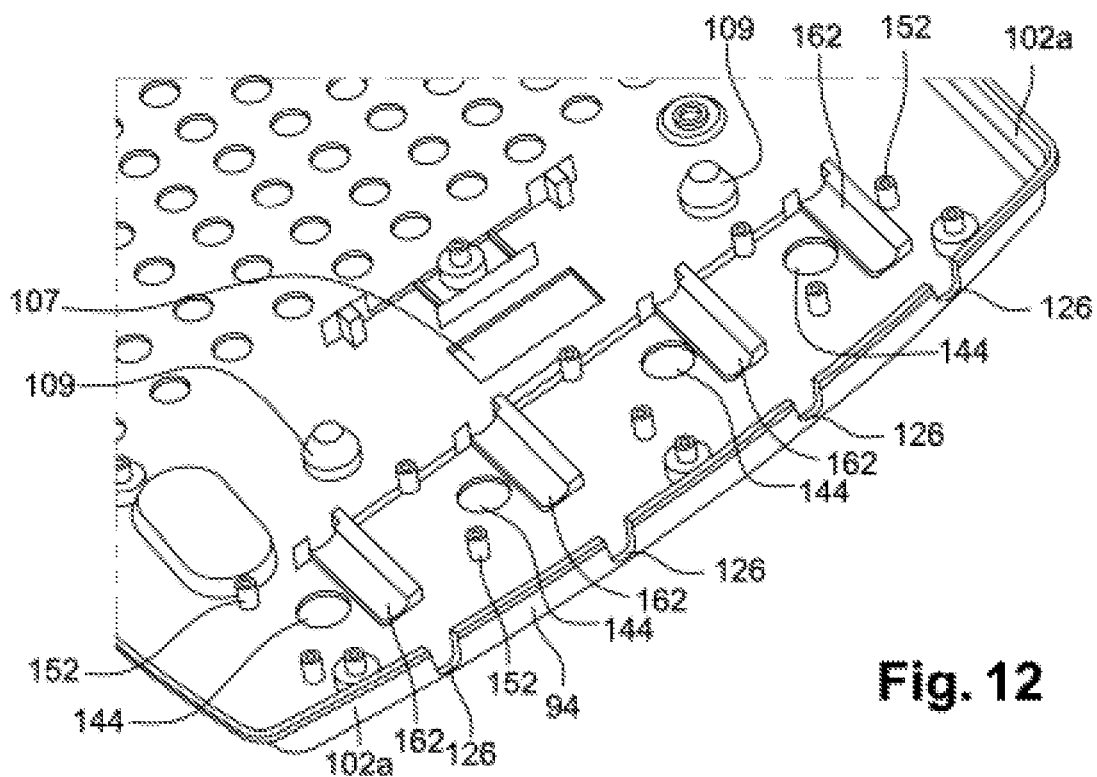
FIG. 12 is a larger-scale schematic view in perspective of the area outlined by dots in FIG. 11.
Figure 13:
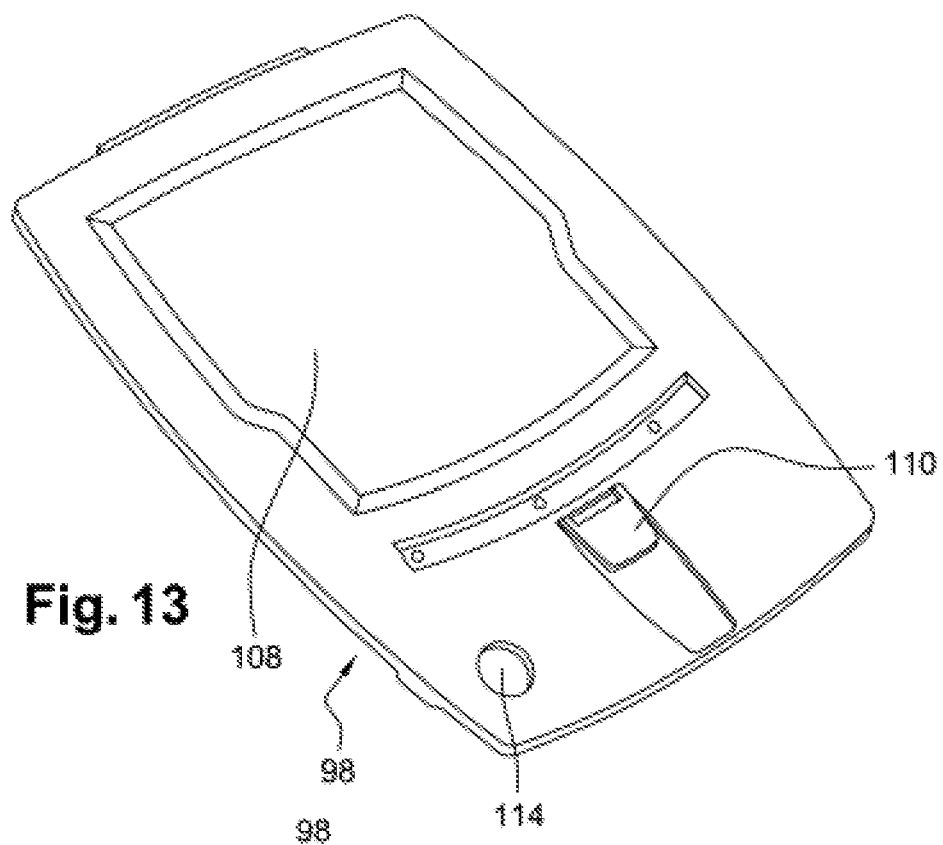
FIGS. 13 and 14 are schematic views in perspective of the upper half-shell.
Figure 14:
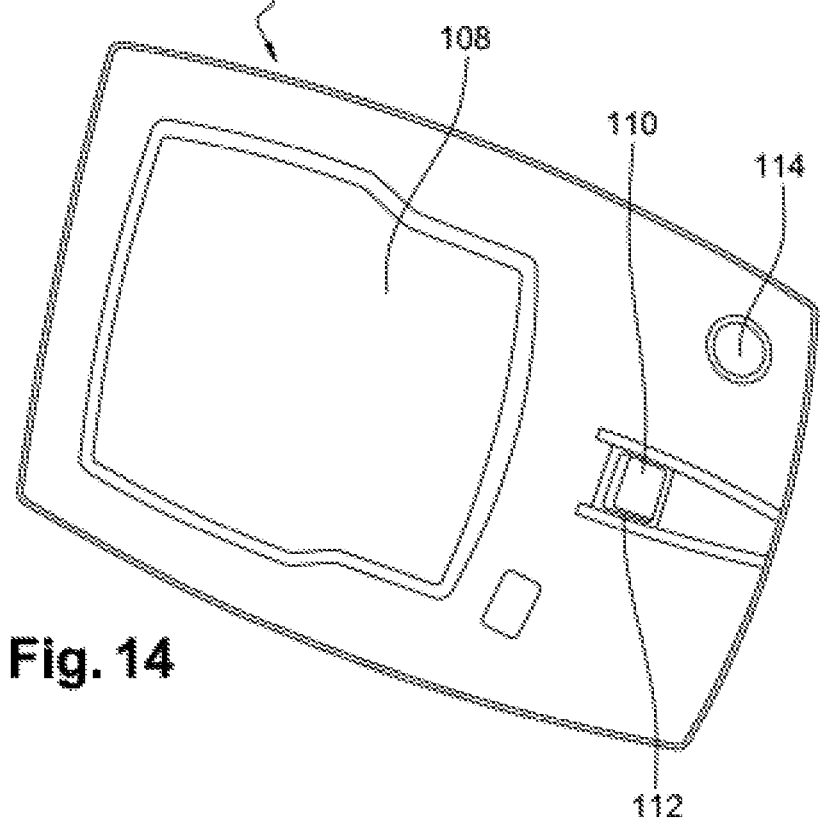

The lower half shell 96 includes a plurality of holes 104 preferably with a diameter of less than 20 mm. For example, cassette 16 is 405 mm long, 305 mm wide and 25 mm thick. It also includes two blind holes 106 spaced from each other and framing a through opening 107. The blind holes 106 are formed by a recess 109 in the lower half-shell 96, extending towards the upper half-shell 98 (FIGS. 11 and 12). The upper half shell 98 comprises an opening or recess 108 whose shape and size are determined to allow the propagation of a wave of the liquid from bag 100 into the opening when the cassette 16 containing a liquid is oscillated about the horizontal axis 63, the opening 108 (or cut-out) being arranged upwardly (FIGS. 7, 13, 14). As mentioned above, the formation of a recess 108 allows the surface of bag 100 inside the housing to be undulated when cassette 16 is mounted in the second position on tray 54 and the tray is moved in an oscillating manner as described in FIGS. 6A, 6B and 6C. The upper half-shell 98 includes an elastic tongue 110 carrying a clip hook 112 with the hook 80 of the frame 72 of the plate 54 as already mentioned above. Hook 112 of the upper half-shell 98 is thus configured to pass through the opening 107 of the lower half-shell 96. Finally, the upper half shell 98 also includes a circular hole 114 for inserting a manual valve actuation plug 116, the use of which will appear more clearly in reference to FIGS. 17 and 18.

It should be noted that the peripheral edge 102a of the lower half-shell 96, located at the first end 92 of the housing 90, has a straight rib 116 which is intended to cooperate with a slot 118 of the support structure 84 of the plate 54 when the cell culture cassette 16 is mounted in its first position on the plate 54 in the enclosure 28 of the incubator 12 (FIGS. 8, 9, 11, 12). In this first position, the clip hook 112 of the upper half-shell 98 passes through the opening 107 of the lower half-shell 96 and cooperates with the hook 80 of the frame 72 of the plate 54 to ensure that the cassette 16 is locked in this first position (FIGS. 3, 4 and 5). To release cassette 16 and remove it from the incubation enclosure 28, one only has to press the tab 110, which leads to disengaging hook 110 of the upper half shell 98 from hook 80 and thus tray 54.

A plate 120 is fixed by snap-fastening into the upper half-shell and is suitable for holding the pipes 36, 38 of the cassette 16 in the folded position on the outer face of the upper half-shell 98.

Figure 10:
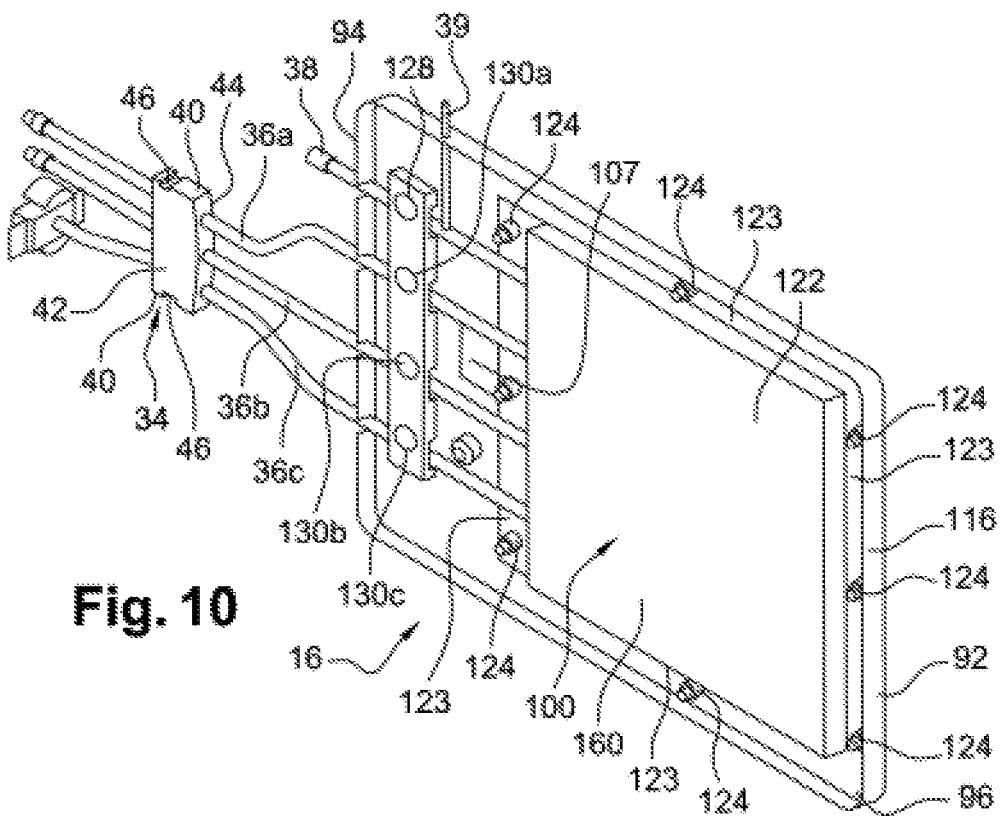
FIG. 10 is a schematic perspective view of the cassette in FIG. 7, with the upper half-shell removed.

FIG. 10 shows the inside of the housing 90, the upper half shell 98 not being shown. As it is visible, cell culture bag 100 has a substantially rectangular shape with a first wall 122 and a second wall (not visible) substantially parallel to each other in the empty and liquid-filled state. The first wall 122 and the second wall are connected and made integral with each other by their peripheral edges 123, by any means such as welding or gluing. In a particular embodiment of the invention, the ratio of the surface area of one of the first wall 122 or second wall to the internal volume of the pocket is between 540 and 600 $cm^2$/L, and is preferably in the order of 580 $cm^2$/L. The distance between the first wall 122 and the second wall is less than 20 mm, preferably between 10 and 20 mm and even more preferably around 14 mm.

The cell culture bag 100 is fixed on the lower half-shell 96 by means of pin 124 projecting from the inner side of the lower half-shell 96. These pins 124 pass through holes in the peripheral edges 123 of cell culture bag 100. The inner volume of bag 100 is in communication with the outside through a plurality of conduits. In particular, cassette 16 can include four ducts or flexible tubing 36, 38, three 36 of which being attached to the bar 34 previously described and a fourth 38 being independent.

More specifically, cassette 16 includes a first and a second sampling tube 36a, 36b and an emptying tube 36c. Tubing 38 corresponds to a tubing for injecting cells of interest. As shown in FIGS. 5, 7, 8, 9 and 10, the cassette also includes a tubing 39 for initial filling of bag 100 with culture medium. In a preferred configuration of the cassette 16 according to the invention, the four tubes 36a, 36b, 36c, 38 are equipped with connectors that can be aseptic connectors and/or needle-free withdrawal connectors, said connectors also including non-return means, as necessary. In the rest of the description, when the reference number 36 is used alone, it will refer to at least one of the pipes 36a, 36b or 36c.

As shown in FIG. 10, tubing 36, 38 extend through notches 126 in the same peripheral edge 120a of the lower half shell 96, namely the peripheral edge 102a formed at the second end 94 of the housing 90. Filler pipe 39 extends on one side adjacent to the side through which the pipes 36, 38 pass and is connected to its end arranged inside the housing 90 in a portion of the pipe 36 arranged fluidly between a valve 128 and bag 100.

Figure 15A:
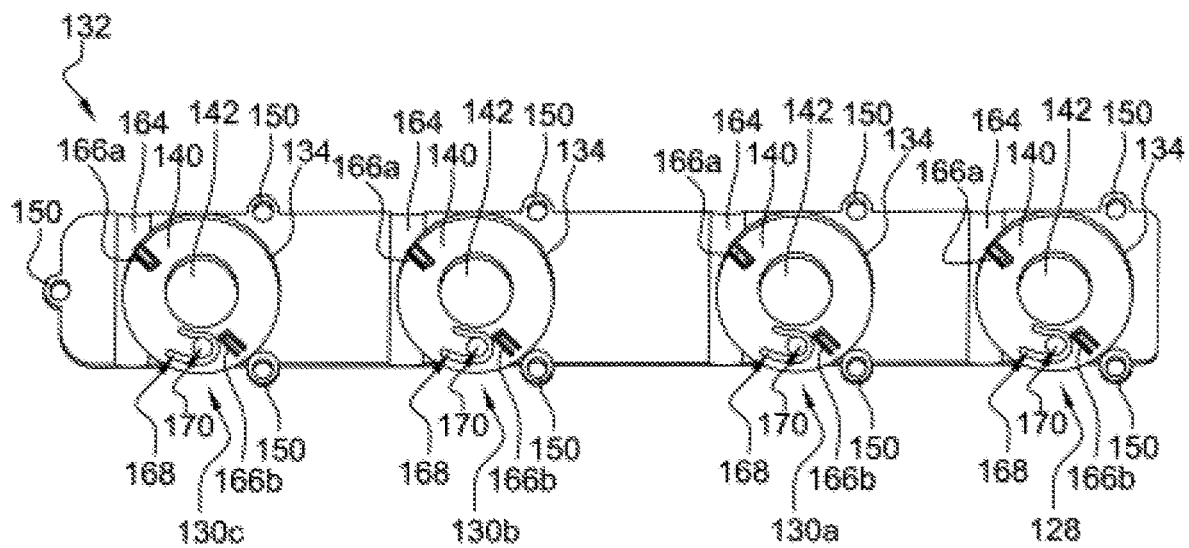
FIG. 15A is a schematic view in perspective of a reception plate for the opening and closing valves of the cassette ducts.

Each of the pipes 36, 38 passes through valves 128, 130a, 130b, 130c for opening/closing the fluid flow through the pipes 36, 38, these pinch valves 128, 130 being arranged in the housing 90. In the example, shown, the three pipes 36 run through a first type of valve 130, the pipe 36a runs through the valve 130a, the pipe 36b runs through the valve 130b and the pipe 36c runs through the valve 130c, while the fourth pipe 38 runs through a second type of valve 128 (FIGS. 10 and 15A). More precisely, the housing 90 comprises a plate 132 (FIGS. 15A, 15B and 15C) having a plurality of substantially cylindrical recesses 134 each receiving a movable member 136, 138 for pinching a tubing 36, 38 (FIGS. 16 and 17). This plate thus forms the body or stator part of the valve 128, 130. Each recess 134 of plate 132 includes an annular bottom wall 140 defining a central hole 142 aligned with a hole 144 of the lower half shell 96 when plate 132 is mounted in the housing 90 (FIGS. 10 and 12).

Figure 9:
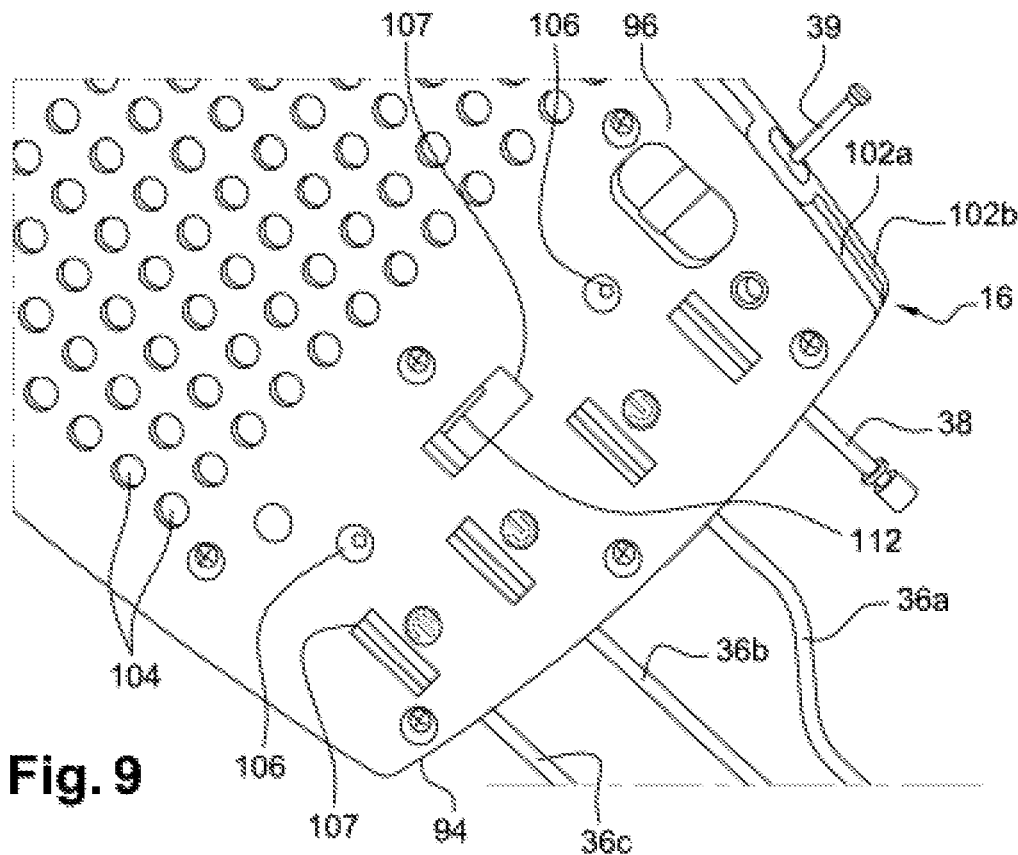
FIG. 9 is a larger scale schematic view of the dotted area in FIG. 8.

Each movable part 136, 138 comprises a lower end 136a, 138a and an upper end 136b, 138b, with reference to the lower half-shell 96 and upper half-shell 98 and with reference to the arrangement of the cassette in relation to the vertical. Of course, it would be possible to more generally designate the lower end as a first end and the upper end as a second end opposite the first end. Thus, the upper end 136b, 138b of each movable member 136, 138 comprises an annular shoulder 146b intended to support along the rotation axis 136c, 138c on the periphery of an orifice 142 of a recess 134 of the plate 132 and surrounding a cylindrical wall 148b intended to fit into the orifice 142 of the recess. In this case, the surface 146b of member 136 is supported on the bottom surface 140 of a recess 134 of a valve 130a, 130b, 130c. It is thus possible to carry out a rotational guidance and centring of the second ends 136b, 136a of the movable parts 136, 138 in the recesses 134 of the plate 132. The lower end 136a, 138a of each movable member 136, 138 comprises an annular shoulder 146a intended to support along the rotation axis 136c, 138c on the periphery of an orifice 144 of the lower half-shell 96 and a cylindrical wall 148a intended to be inserted into orifice 144 of the lower half-shell 96. In this case, the surface 146b of component 138 is supported on the bottom surface 140 of a recess 134 of valve 128. In this way, each of the movable parts 136, 138 is guided in rotation and centred on the lower half-shell 96 and the plate 142, which is itself fixed to the lower half-shell 96 via ears 150 crossed by studs 152 on the inner face of the lower half-shell 96 and thanks to the upper half-shell 98, whose peripheral edges 102b are fixed to the peripheral edges 102a of the lower half-shell 96. The lower ends 136a, 138a of the movable parts 136, 138 thus open through the lower half shell 96 and are thus accessible from the outer face of the lower half shell 96 as shown in FIG. 9.

The movable components 136, as shown in FIGS. 16A, 16B, 16C associated with tubing 36, have at their lower end 136a first coupling means accessible from outside the housing so as to cooperate with the second actuator coupling means 82 of the movable components 136, arranged in the incubator. The first coupling means, formed on the underside of the member 136, here comprise a radial slot 151 whose radially inner end is traversed by the rotation axis 136c and a semi-circular groove 153 centred on the rotation axis 136c. The second coupling means of the actuators 82 can for example comprise two rods 155a, 155b of which a first 155a is centred on the rotation axis of the actuator 82 and a second rod 155b is radially offset with respect to the first rod 155a. When cassette 16 is mounted on frame 72, as shown in FIG. 3A, the first rod 155a engages in the radially inner end of slot 151 while the second rod 155b engages in the semi-circular groove 153. It is understood that the use of a semi-circular groove 153 ensures that the second rod 153b cooperates with groove 153 regardless of the angular position of the movable member 136 before mounting the cassette 16 on the frame 72. The integration of a radial slot 151 on the movable parts 136 allows the movable part 136 to be manually operated if necessary.

In the case of valve 138 in FIGS. 17A and 17B associated with tubing 38, the first coupling means is formed at the upper end 138b of the movable member 138. Unlike the three movable members 136 of the valves 130, the movable member 138 of the valve 128 is not actuated by an electromechanical actuator but manually by a rotating member or knob 154 as shown in FIGS. 18A and 18B. The coupling is made here by a cross recess 157 at the upper end 138b of the movable member 138 in which a complementary cross-shaped member 156 of the actuating button 154 engages. The button 154 is secured to the upper half-shell 98 by means of a plurality of elastically deformable hooks 158 which hang on to the inner periphery of the circular orifice 114 of the upper half-shell 98.

To pinch the tubing 36, 38, each movable member 136, 138 includes a spiral protrusion 160 around the rotation axis 136c, 138c of the movable member 136, 138. The radially outer surface of each protrusion 160 forms a support surface on a tubing 36, 38. Each protrusion 160 has a plane of symmetry in a plane perpendicular to the rotation axis 136c, 138c. Each tubing 36, 38 is partially housed in a rectilinear groove 162 with a semicircular section of the lower half-shell 96 and another part in a rectilinear groove 164 with a semicircular section of the plate 132 so as to pass through the periphery of a recess 134 of the plate 132 in a direction perpendicular to the rotation axis 136c, 138c of the moving part (FIGS. 11, 12, 15A, 15B, 15C). Thus, as a result of the rotation of a movable member 136, 138 of a valve 128, 130, the protrusion 160 ensures the progressive opening or closing of the section of a pipe 36, 38 according to the direction of rotation of the movable member 136, 138.

Figure 15B:
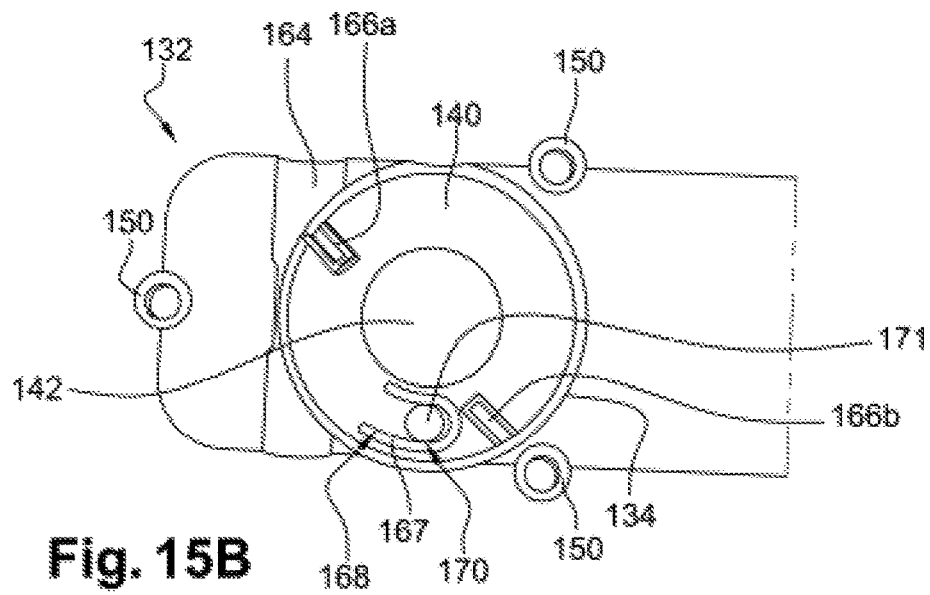
FIGS. 15B and 15C are schematic views in perspective and on a larger scale of only part of the plate shown in FIG. 15A.
Figure 15C:
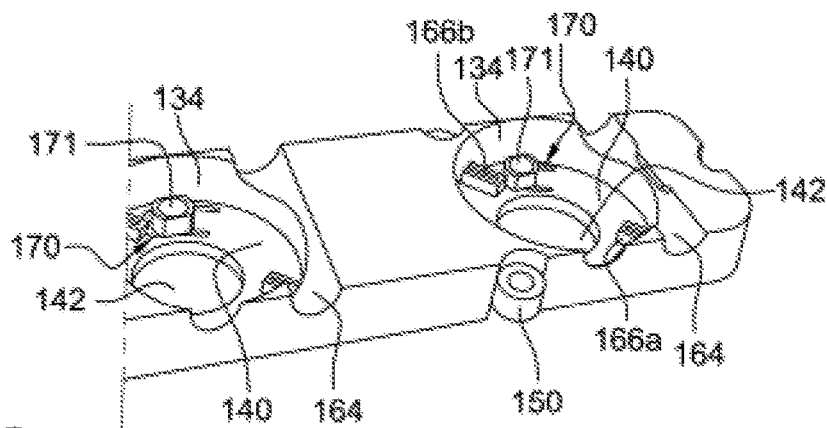
Figure 19A:
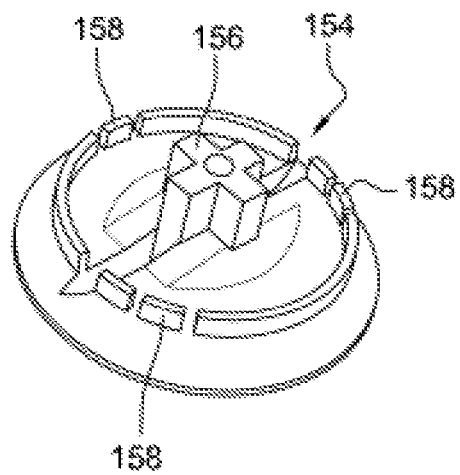
FIGS. 19A and 19B are schematic views of a valve actuator in perspective from FIGS. 17A and 17B.
Figure 19B:
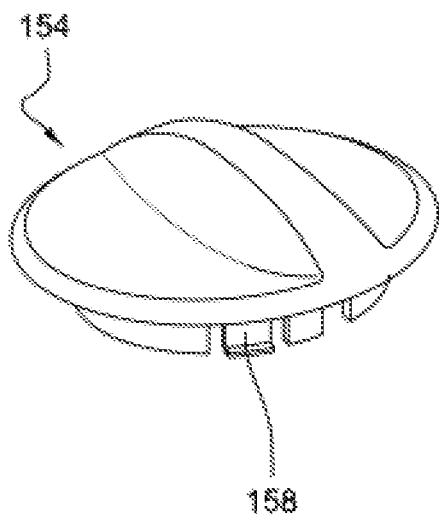

Each annular bottom wall 14D of a recess of the plate 132 carries two stop members 166a, 166b projecting into the interior of the recess 134 and which are angularly spaced from each other. A cut-out 167 is formed in each annular bottom wall 140 of a recess 134 so as to delimit an elastic lamella 168 having a free end carrying a protrusion in the recess 134, this protrusion having a convex portion 171 to cooperate slidingly with moving parts 136, 138 (FIGS. 15B, 15C). The protrusion 170 cooperates slidingly with a groove 172, having a circular arc shape and a concave curved bottom, of each of the movable parts 136, 138. For the movable member 136 in FIGS. 16A, 16B and 16C, groove 172 is formed on a radial annular flange 174 arranged axially between the protrusion 160 and the upper annular shoulder 146b and on the face facing the upper end 136b of the movable member 136. Similarly, for the moving member 138 FIGS. 17A and 17B, groove 172 is formed on a radial annular flange 174 arranged axially between the protrusion 160 and the upper annular shoulder 146b and on the face facing the upper end 138b of the moving member 138.

A semi-spherical cavity 176a, 176b is formed at the angular ends of each groove 170, 172 so as to form stopping positions of the movable member 136, 138 for one corresponding to the opening position where the fluid can flow and for the other corresponding to a closing position where the fluid cannot flow. It is also noted that each movable member 136, 138 includes a radial finger 178 extending laterally from the upper shoulder 146b and is in contact with the face of the flange 174 bearing the groove 172. Thus, in the flow blocking position through the pipes 36, 38, the movable member 136, 138 is positioned so that the protrusion 170 of the elastic lamella 168 is engaged in the cavity or recess 176a of the movable member 136, 138, the radial finger 178 of the movable member 136, 138 being arranged to stop in a counter-clockwise rotation, in FIG. 15, against the stop member 166a. In the position where the flow passes through the pipes 36, 38, the movable member 136, 138 is positioned so that the protrusion 170 of the elastic lamella 168 is engaged in the cavity or recess 176b of the movable member 136, 138, the radial finger 178 of the movable member 136, 138 being arranged to stop in clockwise rotation, in FIG. 15, against the stop member 166b. It is understood that the cooperation of the protrusion 170 with the cavities 176a, 176b makes it possible to ensure elastic locking of the movable parts 136, 138 in the closed and open positions.

It is easy to understand that the valves described above could well be used in other devices requiring devices to open/close the flow of a fluid through a manifold. Therefore, this description also includes any device integrating the valves described, such as for example a device comprising a plate 132 with a plurality of recesses 134 in which rotating parts are engaged.

It would be possible to equip the cassette 16 and/or the incubator with automatic means of checking the correct positioning of cassette 16 in each of its first and second positions. For this purpose, a magnet could be placed inside the housing 90, on the inner side of the lower half-shell 96, this magnet cooperating with two Hall effect sensors appropriately positioned on the plate in relation to the first and second positions to be detected.

Figure 20:
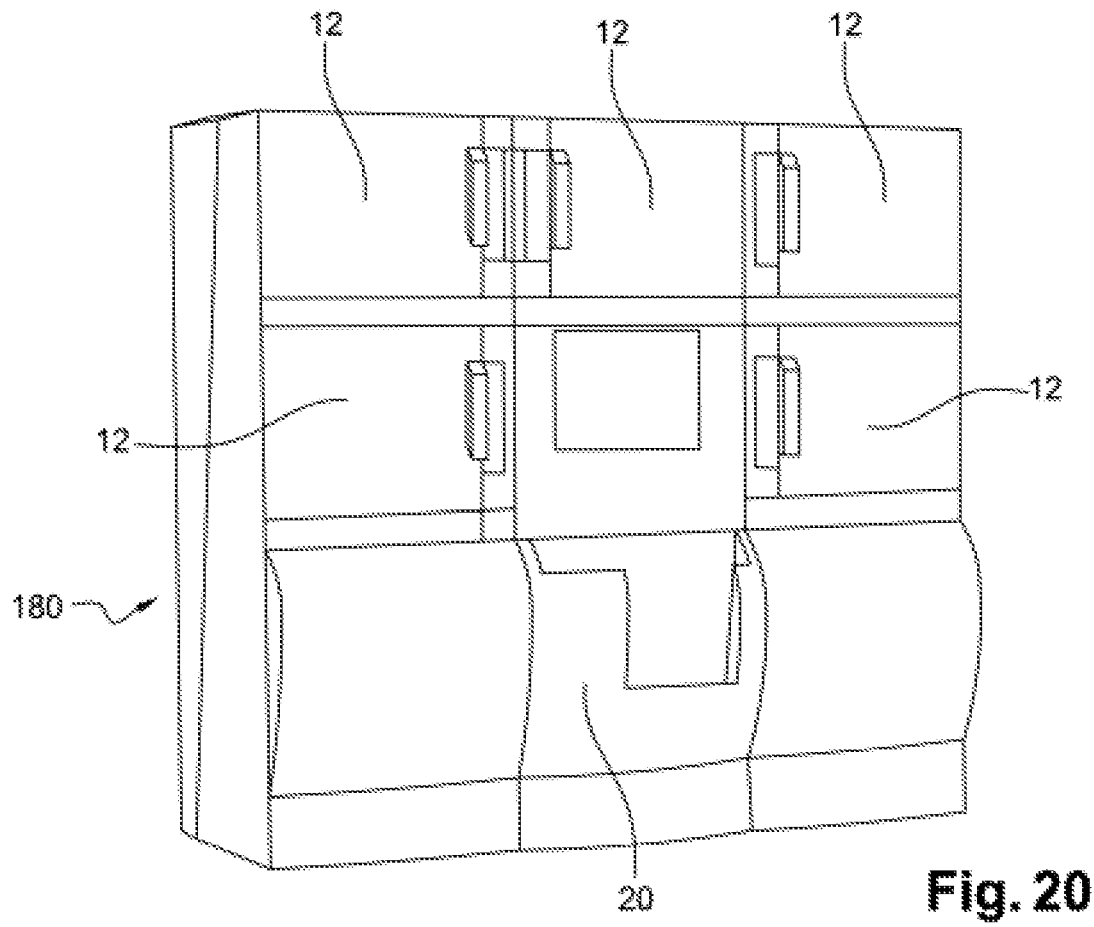
FIG. 20 is a schematic view in perspective of a cell culture system consisting of a plurality of incubators and a centrifuge.

FIG. 20 represents a cell culture system 180 comprising a plurality of incubators 12 as described above and a centrifuge 20. Incubators 12 and centrifuge 20 are controlled by the computer system.

Figure 21:
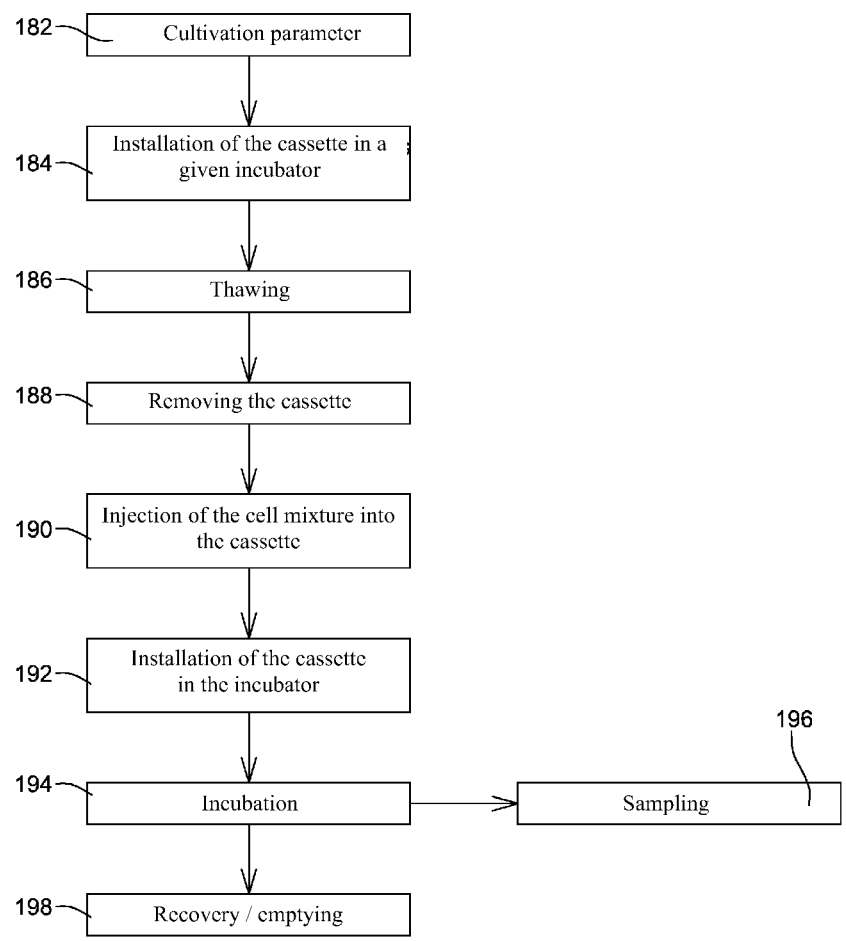
FIG. 21 is an organization chart showing the steps of a cell culture process according to the invention.

FIG. 21 is an organization chart representing the steps of the cell culture process according to the invention.

Prior to the process described below, the cell culture cassette 16 is filled with a cell culture medium using the lateral tubing 38. After filling, this pipe 39 is immediately sealed, for example by welding. The cell culture cassette 16 is then frozen flat, i.e. in a horizontal position, for storage and subsequent use.

A first step in the process 182 is to capture and record culture parameter specific to the biological protocol using the computer system. The entry is made by an operator, the parameters entered being for example the identification of the patient, the identification of the cassette, etc. To facilitate the entry of these parameters, the computer system can be equipped with a bar code reader, the cassette can include a bar code that directly informs the computer system of the number and nature of the cassette. It is then entered by bar code reading or manual entry via the touch screen of the personal identification data indicated on the label of a container, such as a bag, about the cells to be cultured.

In a second step 184, the computer system assigns a given incubator to the operator after checking the availability of the incubator according to a cell culture schedule. The operator installs the cell culture cassette 16 comprising a cell culture liquid in said designated incubator, the other incubators then being, preferably, inaccessible, i.e. doors 22, 30 of the other incubators 12 being locked.

In a third step 186, the process consists in thawing the culture medium housed in the flexible bag of a culture cassette as described above. For this purpose, the cell culture cassette 16, hermetically sealed in a sterile protective envelope, is mounted in the second position on the incubator support and agitation device 52 designated by the computer system, i. e. on the support structure 84 (FIGS. 3A and 3B). The operator closes both doors 22 and 30 and the computer system initiates the thawing procedure, with doors 22 and 30 automatically locked. The support and agitation device is operated in such a way that the cassette 16 is positioned horizontally.

In a fourth step 188, after thawing, the cell culture cassette 16 is extracted from the incubator and the outer shell is removed in an area of adequate controlled activity.

In a fifth step 190, cells of interest, excluding human embryonic stem cells, are injected into the cassette. For this purpose, manual valve 128 is positioned in the open position. It is recalled that tubing 36, 38 are equipped with anti-reflux means to prevent the liquid in bag 100 from flowing out. The cells are injected into bag 100 by means of tubing 38 then valve 128 is positioned in the closed position and tubing 38 is sealed with a tight cap.

In a sixth step 192, cassette 16 filled with culture medium and cells of interest is mounted in its first position corresponding to the incubation position. The strip 34 is mounted in the opening 32 of door 22, the ends of the pipes 36 opposite the bag 100 extending into the opening 38 and being connected to the fluid circuit of the system shown in FIG. 20.

The process according to the invention then includes an incubation step 194 which can last several days and for example about ten days. Periodically, depending on the protocol parameters, the contents of bag 100 can be homogenized, by oscillating the tray 54 around axis 63 as explained above. This homogenization (duration, repetition frequency, amplitude) is determined by the parameters of the selected protocol.

During the incubation step, the operator can take one or more samples 196 from bag 100 (FIGS. 14 and 22). Some of these samplings may be imposed by the computer system. Samples are taken using tubing 36a and 36b.

To take a first sample, the computer system activates the mobile member 136 associated with its corresponding valve 130a in order to allow fluid to flow through the tubing 36a. When the sampling is carried out by the computer system, a final filling operation of tubing 36a is carried out in such a way as to guarantee asepsis and avoid any subsequent use of the sampling tubing already used. The second sampling is done in the same way but by using tubing 36b.

After each sub-step of sampling 196 from bag 100, the operator may carry out analyses of the sample, the results of which may be entered and recorded in the computer system by the operator or automatically.

In a final step of process 198, the computer system recovers or empties the contents of bag 100 of cassette 16.

Finally, the contents of the bag undergo a purification and packaging step in sterile syringes for later use.

The application also concerns a cell culture process, in particular the culture of mammalian cells, in particular human cells, excluding human embryonic stem cells.

These cells, in particular human cells, excluding human embryonic stem cells, may advantageously be, or include, CD34+ (human) cells, in particular CD34+ (human) hematopoietic cells or CD34+ (human) non-hematopoietic cells. These CD34+ (human) cells may, for example, be cells from (human) peripheral blood, (human) umbilical cord or human tissue, particularly (human) peripheral blood.

These cells, in particular human cells, excluding human embryonic stem cells, may advantageously be, or include, stem or progenitor cells, in particular multipotent or pluripotent cells.

These cells are not, or do not include, human embryonic cells.

These cells, in particular human cells, excluding human embryonic stem cells, may advantageously be, or include, human CD34+ (multipotent or pluripotent) stem cells or progenitors of peripheral blood mobilized by a growth factor such as G-CSF (Growth Colony Stimulating Factor).

These cells, in particular human cells, excluding human embryonic stem cells, may be or have been collected from a human subject or patient (newborn, child, adolescent, adult or elderly). The invention is specially adapted to human CD34+ cells (multipotent or pluripotent) that can be collected from the peripheral blood of a human subject or patient. If the patient is to receive chemotherapy, these cells may have been collected before or at the beginning of the chemotherapy.

A biological sample containing cells intended to be cultured (e. g. a sample of (human) blood, in particular a sample of (human) peripheral blood, (human) cord blood or human tissue, in particular a sample of human peripheral blood) is or has been collected from a human subject or patient.

The means of this application have the advantage of not requiring the use of leukapheresis: a simple blood sample, for example a sample of 200 to 250 mL of blood, in particular 220 mL of blood, is sufficient to obtain a significant number of cells, in particular a number of cells that is sufficient for therapeutic and/or preventive treatment, more particularly for autologous or allogeneic cell therapy of a (human) subject or patient, more particularly for autologous cell therapy of the (human) subject or patient.

This is particularly the case for human CD34+ cells intended for therapeutic and/or preventive treatment, more particularly for autologous or allogeneic cell therapy of the subject or patient, more particularly for autologous cell therapy of the subject or patient. Human CD34+ cells may be non-embryonic human CD34+ cells, excluding human embryonic stem cells. Human CD34+ cells are not or do not include embryonic CD34+ cells.

The cell culture means of this application allow to obtain, from a small volume of blood (for example a sample of 200 to 250 mL of blood, in particular 220 mL of blood), a population of at least $10^7$, or at least $10^8$, cells comprising at least 70% of human (non-embryonic) CD34+ cells. In comparison, to obtain such a quantity of human CD34+ cells directly (without cell culture) from the blood of a single subject or patient, it would be necessary to treat a volume of 7 to 10 L of blood by leukapheresis.

Cells that are intended for culture, in particular human (non-embryonic) CD34+ cells, may be purified or isolated from the biological sample collected, including a blood sample, in particular a peripheral blood sample (e.g. a sample of 200 to 250 mL of peripheral blood, in particular 220 mL of peripheral blood).

Cells can be purified to reach a minimum level of a certain cell type. For example, they can be purified to include at least 70% or at least 80% or at least 85% or at least 90% of human (non-embryonic) CD34+ cells, particularly of human CD34+ hematopoietic (non-embryonic) cells.

This isolation or purification can be done by any means known to any person skilled in the art.

For example, for human CD34+ cells, excluding human embryonic stem cells, this isolation or purification may be done using a human anti-CD34 monoclonal antibody, for example the human murine anti-CD34 monoclonal antibody marketed as clone QBEnd-10 (code M7165) by DAKO DENMARK AS (Produktionsvej 42; DK-2600 Glostrup; Denmark). CD34+ (human) cell isolation or purification systems are also commercially available, for example, the ISOLEX 3001 magnetic cell separator marketed by BAXTER (Deerfield, IL, U.S.A.), or the CD34 microbead kit marketed by MILTENYI BIOTECH (2303 Lindbergh Street, Auburn, CA 95602, U.S.A.).

Purified or isolated cells are placed on or in a culture medium whose composition is adapted to the multiplication of these cells. Examples of such culture media, including media suitable for the culture of human CD34+ cells, have been described above. For example, it may be a culture medium as described above, including a medium containing human insulin, human transferrin and human plasma or serum. This culture medium can be contained in the bag of the cassette of this application.

The cells are then placed in incubation, for example by placing the bag, or the cassette containing the bag, in an incubator, including an incubator according to the present application. For example, the incubation time may be several days, in particular 8 to 10 days, in particular 9 days, in particular when it concerns a culture of human CD34+ cells, excluding human embryonic stem cells.

The application also relates to cells, excluding human embryonic stem cells, a cell population comprising such cells, and a pharmaceutical composition comprising such cells or cell population.

These cells or cell populations can be obtained by culture according to this application, as described above.

In this application, cells may include, in particular, (human) CD34+ cells, excluding human embryonic stem cells, in particular (human) hematopoietic CD34+ cells or (human) non-hematopoietic CD34+ cells.

These (human) CD34+ cells may, for example, be cells from (human) peripheral blood, (human) umbilical cord or human tissue, particularly (human) peripheral blood.

These cells may advantageously be, or include, stem or progenitor cells, in particular multipotent or pluripotent cells, excluding human embryonic stem cells.

These cells are not, or do not include, human embryonic cells.

These cells may include, in particular, human CD34+ stem cells or progenitors (multipotent or pluripotent) from peripheral blood mobilized by a growth factor such as G-CSF (Growth Colony Stimulating Factor).

The cells of this application, including the (human) CD34+ cells of the application, excluding human embryonic stem cells, may be in pure or isolated form, or may be included in a cell population.

A cell population according to this application can thus be a population of non-embryonic human cells, which includes human CD34+ cells according to this application.

In particular, cells according to the application may include (a population of) non-embryonic human cells, which are characterized in that:
  they number at least $10^7$ human cells, more particularly at least $10^8$, or at least $1.5 \cdot 10^8$, or from $10^7$ to $1.7 \cdot 10^8$ human cells, and
  they contain at least 70% human CD34+ cells (multipotent or pluripotent, and not embryonic), more particularly at least 80%, or at least 85% or at least 90% human CD34+ cells (multipotent or pluripotent, and not embryonic).

These human cells may also all have the same HLA typing, particularly the same HLA-A, HLA-B, HLA-C and HLA-DR typing.

For example, the cells according to this application may include (a population of) human non-embryonic hematopoietic cells, which are characterized in that:
  they number at least $10^7$ human hematopoietic cells, more particularly at least $10^8$, or at least $1.5 \cdot 10^8$, or from $10^7$ to $1.7 \cdot 10^8$ human hematopoietic cells, and they contain at least 70% human CD34+ cells (multipotent or pluripotent, and not embryonic), more particularly at least 80%, or at least 85% or at least 90% human CD34+ cells (multipotent or pluripotent, and not embryonic).

These human hematopoietic cells may also all have the same HLA typing, particularly the same HLA-A, HLA-B, HLA-C and HLA-DR typing.

The cells of this application may have one or more characteristics, which distinguish them from naive cells.

The term "naive" in this context means that these are cells that have been directly obtained from a human subject or patient, and that may have been purified, but that have not been cultured.

Indeed, it has been observed that after culture in accordance with this application (for example on a culture medium and/or in a bag or cassette as described above), the resulting human cell population differs from the naive population initially placed in culture, in one or more of the following ways:
- a larger average diameter (diameters of 11.2±0.5 µm, in particular 11.18±0.49 µm),
- a higher proportion of CD34− CD14+ cells (monocytes, which can have a positive impact on the effectiveness of a cell transplant),
- a higher proportion (but not 100%) of CD34+ CD33− cells (CD33 being the marker of the myeloid line),
- a smaller proportion (but still greater than 10%) of CD34+ CD133+ cells (marker of endothelial progenitors).

In particular, the cells of this application may be human cells, excluding human embryonic stem cells, that have one or more of the following characteristics:
1/ they number at least $10^7$ human cells, more particularly at least $10^8$, or at least $1.5·10^8$, or from $10^7$ to $1.7·10^8$ human cells,
2/ they all have the same HLA typing, more particularly the same HLA-A, HLA-B, HLA-C and HLA-DR typing,
3/ they contain at least 70% human CD34+ cells (multipotent or pluripotent, and not embryonic), more particularly at least 80%, or at least 85% or at least 90% human CD34+ cells (multipotent or pluripotent, and not embryonic),
4/ they have a cell diameter of 11.2±0.5 µm, in particular 11.18±0.49 µm,
5/ they contain (human) CD34− CD14+ cells in a proportion of 1 to 12%, in particular from 2 to 10% or from 3.8 to 10%,
6/ they contain (human) CD34+ CD33− cells in a proportion of more than 10% or more than 20% or more than 25% (and advantageously less than 100%, in particular less than 60% or less than 50% or less than 40% or less than 35%),
7/ they contain (human) CD34+ CD133+ cells in a proportion of less than 60% or less than 50% (and advantageously more than 20%, in particular more than 25% or more than 30%).

According to an embodiment, the cells of this application are human cells, excluding human embryonic stem cells, which have at least two of these seven characteristics, in particular at least three, or at least four, or at least five, or at least six of these seven characteristics, or have all seven characteristics.

For example, the cells of this application may be human hematopoietic cells, which have one or more of the following characteristics:
1/ they number at least $10^7$ human hematopoietic cells, more particularly at least $10^8$, or at least $1.5·10^8$, or from $10^7$ to $1.7·10^8$ human hematopoietic cells,
2/ they all have the same HLA typing, more particularly the same HLA-A, HLA-B, HLA-C and HLA-DR typing,
3/ they contain at least 70% human CD34+ cells (multipotent or pluripotent, and not embryonic), more particularly at least 80%, or at least 85% or at least 90% human CD34+ cells (multipotent or pluripotent, and not embryonic),
4/ they have a cell diameter of 11.2±0.5 µm, in particular 11.18±0.49 µm,
5/ they contain (human) CD34− CD14+ cells in a proportion of 1 to 12%, in particular from 2 to 10% or from 3.8 to 10%,
6/ they contain (human) CD34+ CD33− cells in a proportion of more than 10% or more than 20% or more than 25% (and advantageously less than 100%, in particular less than 60% or less than 50% or less than 40% or less than 35%),
7/ they contain (human) CD34+ CD133+ cells in a proportion of less than 60% or less than 50% (and advantageously more than 20%, in particular more than 25% or more than 30%).

According to an embodiment, the cells of this application are human hematopoietic cells, which have at least two of these seven characteristics, in particular at least three, or at least four, or at least five, or at least six of these seven characteristics or have all seven characteristics.

In particular, the cells of this application may be human cells, excluding human embryonic stem cells, that have one or more of the following characteristics:
1/ they number at least $10^7$ human cells, more particularly at least $10^8$, or at least $1.5·10^8$, or from $10^7$ to $1.7·10^8$ human cells,
2/ they all have the same HLA typing, more particularly the same HLA-A, HLA-B, HLA-C and HLA-DR typing,
3/ they contain at least 70% human CD34+ cells (multipotent or pluripotent, and not embryonic), more particularly at least 80%, or at least 85% or at least 90% human CD34+ cells (multipotent or pluripotent, and not embryonic),
4/ they have a cell diameter of 11.2±0.5 µm, in particular 11.18±0.49 µm,
5/ they contain (human) CD34− CD14+ cells in a proportion of 1 to 12%, in particular from 2 to 10% or from 3.8 to 10%.

According to an embodiment, the cells of this application are human cells, excluding human embryonic stem cells, which have at least two of these five characteristics, in particular at least three, or at least four of these five characteristics, or all five characteristics.

For example, the cells of this application may be human hematopoietic cells, which have one or more of the following characteristics:
1/ they number at least $10^7$ human hematopoietic cells, more particularly at least $10^8$, or at least $1.5·10^8$, or from $10^7$ to $1.7·10^8$ human hematopoietic cells,
2/ they all have the same HLA typing, more particularly the same HLA-A, HLA-B, HLA-C and HLA-DR typing,
3/ they contain at least 70% human CD34+ cells (multipotent or pluripotent, and not embryonic), more particularly at least 80%, or at least 85% or at least 90% human CD34+ cells (multipotent or pluripotent, and not embryonic), 4/ they have a cell diameter of 11.2±0.5 µm, in particular 11.18±0.49 µm, 5/ they contain (human) CD34− CD14+ cells in a proportion of 1 to 12%, in particular from 2 to 10% or from 3.8 to 10%.

According to an embodiment, the cells of this application are human hematopoietic cells, which have at least two of these five characteristics, in particular at least three, or at least four of these five characteristics, or all five characteristics.

In particular, the cells of this application may be human cells, excluding human embryonic stem cells, which have the following characteristics:

they number at least $10^7$ human cells, more particularly at least $10^8$, or at least $1.5 \cdot 10^8$, or from $10^7$ to $1.7 \cdot 10^8$ human cells, and they comprise at least 70% human CD34+ cells (multipotent or pluripotent, and non-embryonic), more particularly at least 80%, or at least 85% or at least 90% human CD34+ cells (multipotent or pluripotent, and non-embryonic), and which also have at least one or both of the following characteristics:

they have a cell diameter of 11.2±0.5 µm, in particular 11.18±0.49 µm, they contain (human) CD34− CD14+ cells in a proportion of 1 to 12%, in particular from 2 to 10% or from 3.8 to 10%.

For example, the cells of this application may be human hematopoietic cells, which have the following characteristics:

they number at least $10^7$ human hematopoietic cells, more particularly at least $10^8$, or at least $1.5 \cdot 10^8$, or from $10^7$ to $1.7 \cdot 10^8$ human hematopoietic cells, and they contain at least 70% human CD34+ cells (multipotent or pluripotent, and not embryonic), more particularly at least 80%, or at least 85% or at least 90% human CD34+ cells (multipotent or pluripotent, and not embryonic), and which also have at least one (or both) of the following characteristics:

they have a cell diameter of 11.2±0.5 µm, in particular 11.18±0.49 µm, they contain (human) CD34− CD14+ cells in a proportion of 1 to 12%, in particular from 2 to 10% or from 3.8 to 10%.

Cells in this population may all have the same HLA-A, HLA-B, HLA-C and HLA-DR typing.

Cells in this population may also include:

(Human) CD34+ CD33− cells in a proportion of more than 10% or more than 20% or more than 25% (and advantageously less than 100%, in particular less than 60% or less than 50% or less than 40% or less than 35%), (Human) CD34+ CD133+ cells in a proportion of less than 60% or less than 50% (and advantageously more than 20%, in particular more than 25% or more than 30% CD34+ CD133+ cells).

Alternatively or in addition, the cells of this application may have one or more characteristics identical (or not significantly different) to those of naïve cells, in particular naïve human cells, in particular naïve human hematopoietic cells.

Indeed, it has been observed that after culture in accordance with the application (e.g. on a culture medium and/or in a cassette bag as described above), the resulting human cell population (including the resulting human hematopoietic cell population) may have characteristics common to those of the naive (hematopoietic) cell population initially placed in culture.

In particular, the cells of this application may be cells (including hematopoietic cells), which, compared to naïve cells (including naïve hematopoietic cells), and more particularly compared to (naïve) cells initially placed in culture, have one or more of the following characteristics:

1/ the same number or proportion (or not significantly different) of CD34 epitopes, 2/ an identical (or not significantly different) ability to divide, in particular an identical relative length of the telomer (or not significantly different), 3/ the same absence of chromosomal anomalies and polyploidy (or the same chromosomal anomalies or polyploidy, in the same proportions), 4/ identical (or not significantly different) viability, in particular identical (or not significantly different) CD34+ cell viability, for example at least 90% or at least 95% CD34+ cell viability, 5/ an identical (or not significantly different) proportion of CD34− CD2+/CD3+ cells, 6/ an identical (or not significantly different) proportion of CD34− CD19+/CD20+ cells, 7/ an identical (or not significantly different) proportion of CD34− CD56+ cells, 8/ an identical (or not significantly different) proportion of CD34− CD15+ cells.

According to a further embodiment, the cells of this application have at least two, or at least three, or at least four, or at least five, or at least six, or at least seven of these eight characteristics, or have all eight characteristics.

In particular, the cells of this application may be cells (including hematopoietic cells), which, compared to naïve (hematopoietic) cells, in particular compared to initially cultured (naïve) cells, have one or more of the following characteristics:

1/ the same number or proportion (or not significantly different) of CD34 epitopes, 2/ an identical (or not significantly different) ability to divide, in particular an identical relative length of the telomer (or not significantly different), 3/ the same absence of chromosomal anomalies and polyploidy (or the same chromosomal anomalies or polyploidy, in the same proportions).

According to a further embodiment, the cells of this application have at least two of these three characteristics, or all three.

This application explicitly includes any combination of cell characteristics among those described her, including the combination of:

characteristics that differ cells of this application from naive cells, and from characteristics that are identical to those of naive cells.

The means of cell culture of this application correspond essentially to means of ex vivo cell amplification. It has the advantage of providing a significant number (more particularly a therapeutically sufficient number) of autologous or allogeneic cells, in particular autologous cells (more particularly autologous or allogeneic CD34+ cells, more particularly autologous CD34+ cells) from a small sample of peripheral blood from a patient or subject, without introducing harmful modifications in these cells.

Table 1 below provides an illustration of the characteristics of a population of cells obtained from the peripheral blood of a cohort of healthy human volunteers before and after implementation of a culture in a culture bag in accordance with this application (9-day culture on IMDM medium supplemented with glutamine and free of fibroblasts, and containing 0.01 mg/mL insulin, 330 pg/ml transferrin, and 5% (VN) human serum, from cells isolated by sedimentation and purified by immuno-affinity on anti-CD34 magnetic beads):

TABLE 1

| Cohort of 71 Male healthy human volunteers between 21 and 57 years of age Biological sample = 220 ml of peripheral blood per patient | CD34+ cell population | |
| --- | --- | --- |
| | Naive population (as obtained without cell culture) | Example of population obtained after cultivation in accordance with the application (average value per patient, after cell culture) |
| Number of CD34+ cells | From $5.1 \cdot 10^6$ to $40.9 \cdot 10^6$ | From $1 \cdot 10^7$ to $1.7 \cdot 10^8$ |
| Viability of CD34+ cells | More than 95% | More than 95% |
| Cellular diameter of CD34+ | $8.8 \pm 0.1$ μm | $11.18 \pm 0.49$ μm |
| Percentage of CD34+ Cells (after purification) | At least 70% (or at least 80%, or at least 85%, or at least 90%) | At least 70% (or at least 80%, or at least 85%, or at least 90%) |
| CD34− cells CD14+ | From 0.2 to 0.8% | From 3.8 to 10% |
| CD34+ Cells CD33− | 4.2% | 33% |
| CD34+ CD133+ Cells | 75.8% | 44.5% |
| Number of CD34+ epitopes per cell | 14 804 ± 2 294 | 15 363 ± 2 730 |
| Relative length of telomeres | 9.17 ± 1.32% | 8.35 ± 2.07% |
| Chromosomal anomaly | none | none |
| Polyploidy | none | none |
| CD34− CD2+/CD3+ cells | From 0 to 0.3% | From 0 to 1% |
| CD34−C19+/CD20+ cells | From 0 to 0.6% | From 0.1 to 1% |
| CD34− CD56+ cells | 0% | From 0 to 1% |
| CD34− CD15+ cells | From 2 to 5.8% | From 2.5 to 5% |

\* Values from a cohort of 8 volunteers.

Once the culture is complete, the obtained cells, especially the (human) CD34+ cells obtained, can be collected.

The collected cells can be purified or isolated, more particularly purified. In particular, CD34+ cells can be purified, for example by using the means of purification available to the person skilled in the art as indicated above.

The collected and possibly purified cells may be placed in a composition, in particular a pharmaceutical composition, in particular a liquid pharmaceutical composition, for example a non-toxic and isotonic pharmaceutical solution for humans. The resulting composition or solution is a subject of the application.

The composition may include a physiologically acceptable vehicle for humans.

The composition can be formulated to be administrable, more particularly injectable, to or in a human being. It can therefore be liquid and include compounds that are non-toxic to humans, preferably non-toxic compounds at an isotonic concentration for humans.

Thus, in addition to cells, the composition may for example include a buffer solution that is non-toxic to humans, such as a saline phosphate buffer solution (Phosphate Buffer Saline or PBS), or a gluconate and/or acetate buffer solution.

The composition may also include at least one additive that is not toxic to humans, such as a protein from human serum or human plasma, including human serum albumin (HSA).

The composition or solution of the application can be stored until use, for example by cold storage (freezing).

The means of the application may be used for cellular treatment (therapeutic and/or preventive), in particular for autologous or allogeneic cell treatment, advantageously autologous cell treatment.

This cellular treatment may include administration to a patient or subject:
  Of cells of the application, in particular human cells containing CD34+ cells, excluding human embryonic stem cells, as described above, or
  a pharmaceutical composition or solution containing these cells.

This patient or subject may be the same as the one from whom the cells were initially collected for cell culture (autologous cell treatment or therapy). Alternatively, this patient or subject may be different from the one from whom the cells were initially collected for cell culture (allogeneic cell treatment or therapy).

Cellular treatment, more particularly autologous or allogeneic (in particular autologous) cell treatment, may include the treatment or prevention of heart failure or non-cardiac diseases.

Heart failure can be, in particular:
  heart failure, which includes ventricular failure, particularly left ventricular failure,
  especially heart failure with impaired systolic function,
  more particularly cardiac failure with alteration of the contractile function of a ventricle, particularly the left ventricle,
  more specifically, heart failure with increased telesystolic volume associated with a decrease in Left Ventricular Ejection Fraction (LVEF).

This may include heart failure of level II or higher according to the New York Heart Association (NYHA) classification [*The Criteria Committee of the New York Heart Association*]. 1994. Nomenclature and Criteria for Diagnosis of Diseases of the Heart and Great Vessels. $^{(9th}$ edition). Boston: Little, Brown & Co., pages 253-256], particularly level II or higher heart failure (according to NYHA classification) which is induced by mitral regurgitation.

Heart failure can include heart failure induced by
  high blood pressure,
  valve damage,
  a congenital disease,
  refractory angina pectoris (for example, angina pectoris refractory to treatment with Enhanced Extracorporeal CounterPulse (EECCP) or neurostimulation treatment (in particular Transcutaneous NeuroStimulation (TNS) or Spinal Cord Stimulation (SMS), or chelation treatment (in particular EDTA administration treatment),
  cardiomyopathy, in particular
  ischemic cardiomyopathy, in particular myocardial infarction, in particular acute myocardial infarction,
  dilated cardiomyopathy,
  hypertrophic cardiomyopathy,
  restrictive cardiomyopathy, arrhythmogenic Right Ventricular Cardiomyopathy (ARVC). Heart failure may include heart failure induced by cardiomyopathy, in particular by ischemic cardiomyopathy, in particular myocardial infarction, in particular acute myocardial infarction, dilated cardiomyopathy, hypertrophic cardiomyopathy, restrictive cardiomyopathy, arrhythmogenic Right Ventricular Cardiomyopathy (ARVC).

Heart failure may include heart failure induced by cardiomyopathy, in particular ischemic cardiomyopathy, in particular myocardial infarction, in particular acute myocardial infarction.

Heart failure can be treated or prevented, in particular by reducing or even eliminating heart failure and/or limiting the development of heart failure.

Heart failure induced by ischemic cardiomyopathy, in particular myocardial infarction, in particular acute myocardial infarction, can be treated or prevented by reducing or eliminating this heart failure and/or limiting the development of this heart failure.

Indeed, the cells (in particular CD34+ cells) obtained by culture in accordance with this application and possibly by purification, or a pharmaceutical composition or solution containing these cells, may be used for one or more of the following purposes:

reduce or even eliminate post-ischemic myocardial damage, including post-infarction necrosis and/or post-infarction scar size, partially or completely regenerate the structure and/or revascularize the myocardium or infarcted area, improve or restore ventricular function, in particular left ventricular function, in particular ventricular contractility, in particular left ventricular contractility, for example to reduce telesystolic volume in combination with an increase in the left ventricular ejection fraction (LVEF) (in particular to achieve an LVEF of more than 45%).

More specifically, the treatment or prevention of heart failure induced by (acute) myocardial infarction, more particularly (acute) myocardial infarction due to coronary heart disease or heart attack, is targeted. This use is more particularly intended for:

patients with impaired left ventricular function or contractility, and patients have an acute myocardial infarction occurring de novo after a first incident or cardiac syndrome (this first incident or cardiac syndrome may have resulted in stent implantation(s) and percutaneous transluminal coronary angioplasty (PTCA), and/or coronary artery bypass graft surgery (CABG), and who at least 10 days after this first cardiac incident (for example, at least 3 months or at least 6 months after this first cardiac incident or syndrome) have a Left Ventricular Ejection Fraction (LVEF) of 45% or less.

The administration of the cells, of cells or of a pharmaceutical composition or solution of the application may, for example, be carried out within a few weeks, in particular 3 to 6 weeks after an ischemic accident.

The treatment or prevention of heart failure may include cellular cardiomyoplasty (by implanting the cells administered in the infarcted heart zone).

Such treatment or prevention may include administering a population of cells according to this application (including a population of human cells including CD34+ cells, excluding human embryonic stem cells), of cells (including human CD34+ cells, excluding human embryonic stem cells) according to this application, or a composition or solution according to this application, by injecting them by surgery or catheter.

Surgical injection can be an injection directly into the infarcted area, for example, during Coronary Artery Bypass Graft Surgery (CABG).

Catheter injection may include percutaneous transfemoral injection.

The catheter may include an intracoronary, epicardial or transendocardial injection or infusion catheter.

For example, the injection or infusion catheter can be equipped with a helix needle such as the HELIX® catheter marketed by BIOCARDIA® (125 Shoreway Road, Suite B, San Carlos, CA 94070, U.S.A.), which can be coupled to a 2-dimensional (2D) guidance system such as a 2D fluoroscopic guidance system.

The injection or infusion catheter may be, for example, the MYOSTAR® catheter marketed by BIOSENSE WEBSTER, INC. (15715 Arrow Highway; Irwindale; Calif. 91706; U.S.A.).

The injection or infusion catheter can, for example, be coupled to a 3-dimensional (3D) guidance system such as the NOGA® XP electromagnetic 3D cardiac mapping system marketed by BIOLOGICS DELIVERY SYSTEMS GROUP (CORDIS Corp., Diamond Bar, CA U.S.A.).

One or more chemokines, in particular one or more chemokines of the CXC family, in particular the chemokine CXCL12 (Stromal cell-Derived Factor-1 or SDF-1), may be administered, more particularly injected into the patient or subject. Such administration or injection may be simultaneous, joint or delayed in time with respect to the administration, more particularly the injection, of a population of cells according to the application (including a population of human cells including CD34+ cells, excluding human embryonic stem cells), of cells (including human CD34+, excluding human embryonic stem cells) of the application, or a composition or solution of the application.

The uses of the means of the application are not limited to the treatment or prevention of cardiac failure induced by ischemic cardiomyopathy, or cardiac failure induced by chemotherapeutic treatment. The means of the application (in particular the CD34+ means of the application) can alternatively be used to treat or prevent non-cardiac diseases.

It may be a non-cardiac condition, which is not induced by cardiac intervention.

The means of the application can be used to treat myelosuppression, including myelosuppression induced by the treatment of lymphoma, particularly non-Hodgkin's lymphoma, Hodgkin's lymphoma, chronic lymphoid leukaemia. The means of the application may then be used to implant hematopoietic cells (autologous or from another subject), including a population of hematopoietic cells (autologous or allogeneic) containing CD34+ cells, into the patient's bone marrow, by intravenous implantation, as described above. The implanted cells are then used to regenerate the patient's bone marrow.

The means of the application can alternatively be used to treat or prevent a pathology inducing cartilage degeneration, such as osteoarthritis. The means of the application can then be used to implant cells (autologous or from another subject) according to the application into the patient, particularly in the arthritic area, including a population of cells including CD34+ cells, as described above. The implanted cells are then used to regenerate the patient's cartilage.

The means of the application may alternatively be used to treat or prevent hepatic insufficiency, in particular chronic hepatic insufficiency, in particular chronic non-alcoholic hepatic insufficiency (for example to prevent the development of hepatocellular carcinoma). The means of the application may then be used to implant cells (autologous or from another subject) according to the application into the patient, particularly in the hepatic zone, including a population of cells (autologous) including CD34+ cells, as described above. The implanted cells are then used to regenerate the patient's liver.

The term "including", with which "including" or "containing" is synonymous, is an open term, and does not exclude the presence of one or more additional element(s), ingredient(s) or method step(s) that would not be explicitly indicated, while the term "consisting" or "constituted" is a closed term, which excludes the presence of any other additional element, step, or ingredient that is not explicitly stated. The term "consisting essentially" or "essentially constituted" is a partially open term, which does not exclude the presence of one or more additional element(s), ingredient(s) or step(s), insofar as such additional element(s), ingredient(s) or step(s) do not materially affect the basic properties of the invention.

Therefore, the term "including" (or "includes") includes the terms "consisting", "constituted", as well as the terms "essentially consisting" and "essentially constituted".

The invention claimed is:

1. A cell culture cassette designed to be placed into an incubator, the cell culture cassette comprising:
a housing at least partially rigid and internally defining an interior space in which is arranged and fixed a cell culture bag defining an interior volume,
conduits each connected at one end to the interior volume of the bag and each having a second end located outside the housing, and
valves for opening/closing a fluid flow through the conduits that are mounted on the housing, at least some of the valves include a movable member, each movable member including an end accessible from a same outer face of the housing and provided with a first rotating coupling means intending to cooperate with a second rotating coupling means of an actuator.

2. The cell culture cassette according to claim 1, wherein the conduits are formed by flexible tubing and each movable member is configured for pinching the tubing against a structural member of the housing.

3. The cell culture cassette according to claim 2, wherein each movable member comprises a rotation axis and a radially outer periphery of each movable member comprises at least one spiral surface about the rotation axis forming a pinch surface of the tubing so as to vary a fluid passage section through the tubing as the movable member rotates.

4. The cell culture cassette according to claim 3, wherein the movable members are mounted in recesses of a plate arranged inside the housing and integral with the housing, each recess receiving a corresponding movable member.

5. The cell culture cassette according to claim 4, wherein the movable members are centered and rotatably guided at one end into an opening in the housing and at an opposite end into an opening in the plate.

6. The cell culture cassette according to claim 2, wherein the bag has a substantially rectangular shape comprising a first flexible wall and a second flexible wall substantially parallel to each other in both empty and liquid-filled states.

7. The cell culture cassette according to claim 6, wherein a ratio of a sum of surfaces of the first flexible wall and the second flexible wall to a total internal volume of the bag is between 500 and 690 $cm^2/L$.

8. The cell culture cassette according to claim 6, wherein a distance between the first flexible wall and the second flexible wall is less than 20 mm.

9. The cell culture cassette according to claim 1, wherein walls of the bag are permeable to gases.

10. The cell culture cassette according to claim 1, wherein the housing has a shape substantially corresponding to that of a rectangular parallelepiped and comprises a lower half-shell and an upper half-shell fixed with each other, the lower half-shell being rigid and the upper half-shell being rigid or flexible.

11. The cell culture cassette according to claim 10, wherein the upper half shell comprises an opening or central recess whose shape and size are determined to allow propagation of a wave of liquid from a pocket into the opening or central recess when the cell culture cassette containing the liquid is oscillated about a horizontal axis, the opening or central recess being disposed upward.

12. The cell culture cassette according to claim 10, wherein the lower half shell comprises a plurality of holes.

13. The cell culture cassette according to claim 10, wherein the conduits extend through a peripheral edge of one of the lower or upper half-shells.

14. The cell culture cassette according to claim 1, further comprising a conduit support strip, arranged outside the housing and traversed by at least some of the conduits.

15. The cell culture cassette according to claim 1, wherein the bag comprises a cell culture medium.

16. The cell culture cassette according to claim 15, wherein the cell culture medium comprises human insulin, human transferrin, and human plasma or serum.

17. The cell culture cassette according to claim 15, wherein the cell culture medium is frozen.

18. The cell culture cassette according to claim 1, wherein the bag comprises CD34+ cells.

19. The cell culture cassette according to claim 1, wherein the housing has a shape substantially corresponding to that of a rectangular parallelepiped.

20. The cell culture cassette according to claim 1, wherein the housing comprises a plurality of holes on said same outer face of the housing.

21. A cell culture incubator comprising a thermostatic enclosure and a support and agitation device for supporting and agitating a cell culture cassette according to claim 1 and means for positioning and locking the cell culture cassette in a given position in the support and agitation device.

22. The incubator according to claim 21, wherein the support and agitation device comprises a tray for supporting the cell culture cassette which is rotatably mounted around a horizontal axis about which the tray is configured to oscillate for agitating and homogenizing contents of the bag.

23. The incubator according to claim 22, wherein the support and agitation device comprises a connecting rod, an upper end of which is connected via an oscillator to a plate and a lower end of which is connected to a crank rotatably driven by a shaft of a motor whose axis is substantially horizontal.

24. The incubator according to claim 22, wherein the tray carries electromechanical actuators for opening/closing the valves, one outlet of which carries a second coupling means for cooperating with a first coupling means of the valves of the cell culture cassette when the cell culture cassette is in said given position.

25. The incubator according to claim 21, further comprising a door for sealing an opening of the enclosure, said opening comprising a peripheral edge in which a recess is formed whose shape is adapted to receive a conduit support strip for the conduits of the cell culture cassette, the conduit support strip forming a sealing member between the door and the peripheral edge when the door is in a closed position of the enclosure.

26. The incubator according to claim 21, further comprising means for controlling a position of the cell culture cassette in the support and agitation device.

27. A cell culture automated apparatus comprising at least one incubator according to claim 21, and a computer control system including data capture and recording means for regulating culture conditions in the enclosure of said at least one incubator and for controlling the valves of the cell culture cassette.

28. A method of cell culture by means of an automated apparatus according to claim 27, the method comprising:
    a) placing the cell culture cassette inside the enclosure in a thawing position on the support and agitation device;
    b) feeding the bag with cells to be cultured;
    c) placing the cell culture cassette on the support and agitation device in a cell culture position;
    d) agitating the cell culture cassette for a given period of time to homogenize its contents;
    e) maintaining the cell culture cassette under incubation conditions for several days; and
    f) recovering the contents of the cell culture cassette by means of one of the conduits of the cell culture cassette.

29. The method according to claim 28, wherein the method comprises:
    during step d), one or more sampling steps for sampling the contents of the bag, each sampling step preceded by a step of tilting the tray from a horizontal culture position to an inclined position in which a sampling area of the bag represents a lowest point of the bag.

30. The method according to claim 28, wherein the cells to be cultured are CD34+ cells.

31. A pharmaceutical composition for use in a treatment of heart failure induced by myocardial infarction, wherein the composition comprises cells capable of being produced by culture in the cell culture cassette according to claim 1, said cells:
    being human cells,
    being at least $10^7$ cells in number,
    containing at least 70% human CD34+ cells,
    comprising human CD34− CD14+ cells in a proportion of 1 to 12%, and/or
    having a cell diameter of 11.2±0.5 μm.

* * * * *

UNITED STATES PATENT AND TRADEMARK OFFICE
CERTIFICATE OF CORRECTION

PATENT NO. : 11,840,682 B2
APPLICATION NO. : 16/312434
DATED : December 12, 2023
INVENTOR(S) : Valat et al.

Page 1 of 1

It is certified that error appears in the above-identified patent and that said Letters Patent is hereby corrected as shown below:

In the Claims

Column 28,
Lines 17 and 24, in Claims 11 and 12, "half shell" should read --half-shell--.

Signed and Sealed this
Seventh Day of January, 2025

Derrick Brent
*Acting Director of the United States Patent and Trademark Office*